(12) United States Patent
Laird et al.

(10) Patent No.: US 6,331,393 B1
(45) Date of Patent: Dec. 18, 2001

(54) PROCESS FOR HIGH-THROUGHPUT DNA METHYLATION ANALYSIS

(75) Inventors: Peter W. Laird; Cindy A. Eads, both of South Pasadena; Kathleen D. Danenberg, Altadena, all of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/311,912

(22) Filed: May 14, 1999

(51) Int. Cl.$^7$ ..................................................... C12Q 1/68
(52) U.S. Cl. .................................. 435/6; 435/91.2
(58) Field of Search ........................ 435/6, 91.2, 91.21; 536/24.31, 24.33

(56) References Cited

U.S. PATENT DOCUMENTS 5,786,146 * 7/1998 Herman et al. ........................... 435/6
6,017,704 * 7/1998 Herman et al. ........................... 453/6

OTHER PUBLICATIONS

Xiong et al. Nucleic Acids Research 25(12):2532–2534, 1997.*
Gonzalgo et al. Nucleic Acids Research 25(12): 2529–2531, 1997.*

* cited by examiner

*Primary Examiner*—Lisa B. Arthur
(74) *Attorney, Agent, or Firm*—Barry L. Davison; Davis Wright Tremaine LLP

(57) ABSTRACT

There is disclosed an improved high-throughput and quantitative process for determining methylation patterns in genomic DNA samples based on amplifying modified nucleic acid, and detecting methylated nucleic acid based on amplification-dependent displacement of specifically annealed hybridization probes. Specifically, the inventive process provides for treating genomic DNA samples with sodium bisulfite to create methylation-dependent sequence differences, followed by detection with fluorescence-based quantitative PCR techniques. The process is particularly well suited for the rapid analysis of a large number of nucleic acid samples, such as those from collections of tumor tissues.

26 Claims, 9 Drawing Sheets

Methylation Analysis of the *ESR1* Gene

| DNA | COBRA (% One or Two Sites Methylated) | MethyLight (Ratio of Methylated / Control) | MethyLight (Ratio of Unmethylated / Control) |
|---|---|---|---|
| *Bisulfite Treated* | | | |
| Sperm | 0% | 0 | 62 |
| HCT116 | 95% | 36 | 0 |
| *Untreated* | | | |
| Sperm | No PCR | 0 | 0 |
| HCT116 | No PCR | 0 | 0 |

*Fig. 5B*

PROCESS FOR HIGH-THROUGHPUT DNA METHYLATION ANALYSIS

TECHNICAL FIELD OF THE INVENTION

The present invention provides an improved high-throughput and quantitative process for determining methylation patterns in genomic DNA samples. Specifically, the inventive process provides for treating genomic DNA samples with sodium bisulfite to create methylation-dependent sequence differences, followed by detection with fluorescence-based quantitative PCR techniques.

BACKGROUND OF THE INVENTION

In higher order eukaryotic organisms, DNA is methylated only at cytosines located 5' to guanosine in the CpG dinucleotide. This modification has important regulatory effects on gene expression predominantly when it involves CpG rich areas (CpG islands) located in the promoter region of a gene sequence. Extensive methylation of CpG islands has been associated with transcriptional inactivation of selected imprinted genes and genes on the inactive X chromosome of females. Aberrant methylation of normally unmethylated CpG islands has been described as a frequent event in immortalized and transformed cells and has been frequently associated with transcriptional inactivation of tumor suppressor genes in human cancers.

DNA methylases transfer methyl groups from a universal methyl donor, such as S-adenosyl methionine, to specific sites on the DNA. One biological function of DNA methylation in bacteria is protection of the DNA from digestion by cognate restriction enzymes. Mammalian cells possess methylases that methylate cytosine residues on DNA that are 5' neighbors of guanine (CpG). This methylation may play a role in gene inactivation, cell differentiation, tumorigenesis, X-chromosome inactivation, and genomic imprinting. CpG islands remain unmethylated in normal cells, except during X-chromosome inactivation and parental specific imprinting where methylation of 5' regulatory regions can lead to transcriptional repression. DNA methylation is also a mechanism for changing the base sequence of DNA without altering its coding function. DNA methylation is a heritable, reversible and epigenetic change. Yet, DNA methylation has the potential to alter gene expression, which has profound developmental and genetic consequences.

The methylation reaction involves flipping a target cytosine out of an intact double helix to allow the transfer of a methyl group from S-adenosylmethionine in a cleft of the enzyme DNA (cystosine-5)-methyltransferase (Klimasauskas et al., *Cell* 76:357–369, 1994) to form 5-methylcytosine (5-mCyt). This enzymatic conversion is the only epigenetic modification of DNA known to exist in vertebrates and is essential for normal embryonic development (Bird, *Cell* 70:5–8, 1992; Laird and Jaenisch, *Human Mol. Genet.* 3:1487–1495, 1994; and Li et al., *Cell* 69:915–926, 1992). The presence of 5-mCyt at CpG dinucleotides has resulted in a 5-fold depletion of this sequence in the genome during vertebrate evolution, presumably due to spontaneous deamination of 5-mCyt to T (Schoreret et al., *Proc. Natl. Acad Sci. USA* 89:957–961, 1992). Those areas of the genome that do not show such suppression are referred to as "CpG islands" (Bird, *Nature* 321:209–213, 1986; and Gardiner-Garden et al., *J. Mol. Biol.* 196:261–282, 1987). These CpG island regions comprise about 1% of vertebrate genomes and also account for about 15% of the total number of CpG dinucleotides (Bird, *Nature* 321:209–213, 1986). CpG islands are typically between 0.2 to about 1 kb in length and are located upstream of many housekeeping and tissue-specific genes, but may also extend into gene coding regions. Therefore, it is the methylation of cytosine residues within CpG islands in somatic tissues, which is believed to affect gene function by altering transcription (Cedar, *Cell* 53:3–4, 1988).

Methylation of cytosine residues contained within CpG islands of certain genes has been inversely correlated with gene activity. This could lead to decreased gene expression by a variety of mechanisms including, for example, disruption of local chromatin structure, inhibition of transcription factor-DNA binding, or by recruitment of proteins which interact specifically with methylated sequences indirectly preventing transcription factor binding. In other words, there are several theories as to how methylation affects mRNA transcription and gene expression, but the exact mechanism of action is not well understood. Some studies have demonstrated an inverse correlation between methylation of CpG islands and gene expression, however, most CpG islands on autosomal genes remain unmethylated in the germline and methylation of these islands is usually independent of gene expression. Tissue-specific genes are usually unmethylated in the receptive target organs but are methylated in the germline and in non-expressing adult tissues. CpG islands of constitutively-expressed housekeeping genes are normally unmethylated in the germline and in somatic tissues.

Abnormal methylation of CpG islands associated with tumor suppressor genes may also cause decreased gene expression. Increased methylation of such regions may lead to progressive reduction of normal gene expression resulting in the selection of a population of cells having a selective growth advantage (i.e., a malignancy).

It is considered that an altered DNA methylation pattern, particularly methylation of cytosine residues, causes genome instability and is mutagenic. This, presumably, has led to an 80% suppression of a CpG methyl acceptor site in eukaryotic organisms, which methylate their genomes. Cytosine methylation further contributes to generation of polymorphism and germ-line mutations and to transition mutations that inactivate tumor-suppressor genes (Jones, *Cancer Res.* 56:2463–2467, 1996). Methylation is also required for embryonic development of mammals (Li et al., *Cell* 69:915–926, 1992). It appears that the methylation of CpG-rich promoter regions may be blocking transcriptional activity. Ushijima et al. (*Proc. Natl. Acad Sci. USA* 94:2284–2289, 1997) characterized and cloned DNA fragments that show methylation changes during murine hepatocarcinogenesis. Data from a group of studies of altered methylation sites in cancer cells show that it is not simply the overall levels of DNA methylation that are altered in cancer, but changes in the distribution of methyl groups.

These studies suggest that methylation at CpG-rich sequences, known as CpG islands, provide an alternative pathway for the inactivation of tumor suppressors. Methylation of CpG oligonucleotides in the promoters of tumor suppressor genes can lead to their inactivation. Other studies provide data that alterations in the normal methylation process are associated with genomic instability (Lengauer et al. *Proc. Natl. Acad. Sci. USA* 94:2545–2550, 1997). Such abnormal epigenetic changes may be found in many types of cancer and can serve as potential markers for oncogenic transformation, provided that there is a reliable means for rapidly determining such epigenetic changes. Therefore, there is a need in the art for a reliable and rapid (high-throughput) method for determining methylation as the preferred epigenetic alteration.

METHODS TO DETERMINE DNA METHYLATION

There are a variety of genome scanning methods that have been used to identify altered methylation sites in cancer cells. For example, one method involves restriction landmark genomic scanning (Kawai et al., *Mol. Cell. Biol.* 14:7421–7427, 1994), and another example involves methylation-sensitive arbitrarily primed PCR (Gonzalgo et al., *Cancer Res.* 57:594–599, 1997). Changes in methylation patterns at specific CpG sites have been monitored by digestion of genomic DNA with methylation-sensitive restriction enzymes followed by Southern analysis of the regions of interest (digestion-Southern method). The digestion-Southern method is a straightforward method but it has inherent disadvantages in that it requires a large amount of high molecular weight DNA (at least or greater than 5 µg) and has a limited scope for analysis of CpG sites (as determined by the presence of recognition sites for methylation-sensitive restriction enzymes). Another method for analyzing changes in methylation patterns involves a PCR-based process that involves digestion of genomic DNA with methylation-sensitive restriction enzymes prior to PCR amplification (Singer-Sam et al., *Nucl. Acids Res.* 18:687, 1990). However, this method has not been shown effective because of a high degree of false positive signals (methylation present) due to inefficient enzyme digestion or overamplification in a subsequent PCR reaction.

Genomic sequencing has been simplified for analysis of DNA methylation patterns and 5-methylcytosine distribution by using bisulfite treatment (Frommer et al., *Proc. Natl. Acad Sci. USA* 89:1827–1831, 1992). Bisulfite treatment of DNA distinguishes methylated from unmethylated cytosines, but original bisulfite genomic sequencing requires large-scale sequencing of multiple plasmid clones to determine overall methylation patterns, which prevents this technique from being commercially useful for determining methylation patterns in any type of a routine diagnostic assay.

In addition, other techniques have been reported which utilize bisulfite treatment of DNA as a starting point for methylation analysis. These include methylation-specific PCR (MSP) (Herman et al. *Proc. Natl. Acad Sci. USA* 93:9821–9826, 1992); and restriction enzyme digestion of PCR products amplified from bisulfite-converted DNA (Sadri and Hornsby, *Nucl. Acids Res.* 24:5058–5059, 1996; and Xiong and Laird, *Nucl. Acids Res.* 25:2532–2534, 1997).

PCR techniques have been developed for detection of gene mutations (Kuppuswamy et al., *Proc. Natl. Acad. Sci. USA* 88:1143–1147, 1991) and quantitation of allelic-specific expression (Szabo and Mann, *Genes Dev.* 9:3097–3108, 1995; and Singer-Sam et al., PCR *Methods Appl.* 1:160–163, 1992). Such techniques use internal primers, which anneal to a PCR-generated template and terminate immediately 5' of the single nucleotide to be assayed. However an allelic-specific expression technique has not been tried within the context of assaying for DNA methylation patterns.

Most molecular biological techniques used to analyze specific loci, such as CpG islands in complex genomic DNA, involve some form of sequence-specific amplification, whether it is biological amplification by cloning in *E. coli*, direct amplification by PCR or signal amplification by hybridization with a probe that can be visualized. Since DNA methylation is added post-replicatively by a dedicated maintenance DNA methyltransferase that is not present in either *E. coli* or in the PCR reaction, such methylation information is lost during molecular cloning or PCR amplification. Moreover, molecular hybridization does not discriminate between methylated and unmethylated DNA, since the methyl group on the cytosine does not participate in base pairing. The lack of a facile way to amplify the methylation information in complex genomic DNA has probably been a most important impediment to DNA methylation research. Therefore, there is a need in the art to improve upon methylation detection techniques, especially in a quantitative manner.

The indirect methods for DNA methylation pattern determinations at specific loci that have been developed rely on techniques that alter the genomic DNA in a methylation-dependent manner before the amplification event. There are two primary methods that have been utilized to achieve this methylation-dependent DNA alteration. The first is digestion by a restriction enzyme that is affected in its activity by 5-methylcytosine in a CpG sequence context. The cleavage, or lack of it, can subsequently be revealed by Southern blotting or by PCR. The other technique that has received recent widespread use is the treatment of genomic DNA with sodium bisulfite. Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. The resulting sequence difference has been detected using standard DNA sequence detection techniques, primarily PCR.

Many DNA methylation detection techniques utilize bisulfite treatment. Currently, all bisulfite treatment-based methods are followed by a PCR reaction to analyze specific loci within the genome. There are two principally different ways in which the sequence difference generated by the sodium bisulfite treatment can be revealed. The first is to design PCR primers that uniquely anneal with either methylated or unmethylated converted DNA. This technique is referred to as "methylation specific PCR" or "MSP". The method used by all other bisulfite-based techniques (such as bisulfite genomic sequencing, COBRA and Ms-SNuPE) is to amplify the bisulfite-converted DNA using primers that anneal at locations that lack CpG dinucleotides in the original genomic sequence. In this way, the PCR primers can amplify the sequence in between the two primers, regardless of the DNA methylation status of that sequence in the original genomic DNA. This results in a pool of different PCR products, all with the same length and differing in their sequence only at the sites of potential DNA methylation at CpGs located in between the two primers. The difference between these methods of processing the bisulfite-converted sequence is that in MSP, the methylation information is derived from the occurrence or lack of occurrence of a PCR product, whereas in the other techniques a mix of products is always generated and the mixture is subsequently analyzed to yield quantitative information on the relative occurrence of the different methylation states.

MSP is a qualitative technique. There are two reasons that it is not quantitative. The first is that methylation information is derived from the comparison of two separate PCR reactions (the methylated and the unmethylated version). There are inherent difficulties in making kinetic comparisons of two different PCR reactions. The other problem with MSP is that often the primers cover more than one CpG dinucleotide. The consequence is that multiple sequence variants can be generated, depending on the DNA methylation pattern in the original genomic DNA. For instance, if the forward primer is a 24-mer oligonucleotide that covers 3 CpGs, then $2^3=8$ different theoretical sequence permutations could arise in the genomic DNA following bisulfite conversion within this 24-nucleotide sequence. If only a fully methylated and a fully unmethylated reaction is run, then you are really only investigating 2 out of the 8 possible methylation states. The situation is further complicated if the intermediate methylation states lead to amplification, but with reduced efficiency. Therefore, the MSP technique is non-quantitative. Therefore, there is a need in the art to improve the MSP technique and change it to be more quantitative and facilitate its process to greater throughput. The present invention addresses this need for a more rapid and quantitative methylation assay.

SUMMARY OF THE INVENTION

The present invention provides a method for detecting a methylated CpG island within a genomic sample of DNA comprising:

(a) contacting a genomic sample of DNA from a patient with a modifying agent that modifies unmethylated cytosine to produce a converted nucleic acid;

(b) amplifying the converted nucleic acid by means of two oligonucleotide primers in the presence or absence of one or a plurality of specific oligonucleotide probes, wherein one or more of the oligonucleotide primers and/or probes are capable of distinguishing between unmethylated and methylated nucleic acid; and (c) detecting the methylated nucleic acid based on amplification-mediated displacement of the probe. Preferably, the amplifying step is a polymerase chain reaction (PCR) and the modifying agent is bisulfite. Preferably, the converted nucleic acid contains uracil in place of unmethylated cytosine residues present in the unmodified genomic sample of DNA. Preferably, the probe further comprises a fluorescence label moiety and the amplification and detection step comprises fluorescence-based quantitative PCR.

The invention provides a method for detecting a methylated CpG-containing nucleic acid comprising:

(a) contacting a nucleic acid-containing sample with a modifying agent that modifies unmethylated cytosine to produce a converted nucleic acid;

(b) amplifying the converted nucleic acid in the sample by means of oligonucleotide primers in the presence of a CpG-specific oligonucleotide probe, wherein the CpG-specific probe, but not the primers, distinguish between modified unmethylated and methylated nucleic acid; and (c) detecting the methylated nucleic acid based upon an amplification-mediated displacement of the CpG-specific probe. Preferably, the amplifying step comprises a polymerase chain reaction (PCR) and the modifying agent comprises bisulfite. Preferably, the converted nucleic acid contains uracil in place of unmethylated cytosine residues present in the unmodified nucleic acid-containing sample. Preferably, the detection method is by means of a measurement of a fluorescence signal based on amplification-mediated displacement of the CpG-specific probe and the amplification and detection method comprises fluorescence-based quantitative PCR. The methylation amounts in the nucleic acid sample are quantitatively determined based on reference to a control reaction for amount of input nucleic acid.

The present invention further provides a method for detecting a methylated CpG-containing nucleic acid comprising:

(a) contacting a nucleic acid-containing sample with a modifying agent that modifies unmethylated cytosine to produce a converted nucleic acid;

(b) amplifying the converted nucleic acid in the sample by means of oligonucleotide primers and in the presence of a CpG-specific oligonucleotide probe, wherein both the primers and the CpG-specific probe distinguish between modified unmethylated and methylated nucleic acid; and (c) detecting the methylated nucleic acid based on amplification-mediated displacement of the CpG-specific probe. Preferably, the amplifying step is a polymerase chain reaction (PCR) and the modifying agent is bisulfite. Preferably, the converted nucleic acid contains uracil in place of unmethylated cytosine residues present in the unmodified nucleic acid-containing sample. Preferably, the detection method comprises measurement of a fluorescence signal based on amplification-mediated displacement of the CpG-specific probe and the amplification and detection method comprises fluorescence-based quantitative PCR.

The present invention further provides a methylation detection kit useful for the detection of a methylated CpG-containing nucleic acid comprising a carrier means being compartmentalized to receive in close confinement therein one or more containers comprising:

(i) a first container containing a modifying agent that modifies unmethylated cytosine to produce a converted nucleic acid;

(ii) a second container containing primers for amplification of the converted nucleic acid;

(iii) a third container containing primers for the amplification of control unmodified nucleic acid; and (iv) a fourth container containing a specific oligonucleotide probe the detection of which is based on amplification-mediated displacement, wherein the primers and probe each may or may not distinguish between unmethylated and methylated nucleic acid. Preferably, the modifying agent comprises bisulfite. Preferably, the modifying agent converts cytosine residues to uracil residues. Preferably, the specific oligonucleotide probe is a CpG-specific oligonucleotide probe, wherein the probe, but not the primers for amplification of the converted nucleic acid, distinguishes between modified unmethylated and methylated nucleic acid. Alternatively, the specific oligonucleotide probe is a CpG-specific oligonucleotide probe, wherein both the probe and the primers for amplification of the converted nucleic acid, distinguish between modified unmethylated and methylated nucleic acid. Preferably, the probe further comprises a fluorescent moiety linked to an oligonucleotide base directly or through a linker moiety and the probe is a specific, dual-labeled TaqMan probe.

BRIEF DESCRIPTION OF THE DRAWINGS

FIG. 5A–5B shows a comparison of the inventive assay to a conventional COBRA assay. Panel A shows a COBRA gel used to determine the level of DNA methylation at the ESR1 locus in DNAs of known methylation status (sperm, unmethylated) and HCT116 (methylated). The relative amounts of the cleaved products are indicated below the gel. A 56-bp fragment represents DNA molecules in which the TaqI site proximal to the hybridization probe is methylated in the original genomic DNA. The 86-bp fragment represents DNA molecules in which the proximal TaqI site is unmethylated and the distal site is methylated. Panel B summarizes the COBRA results and compares them to results obtained with the methylated and unmethylated version of the inventive assay process. The results are expressed as ratios between the methylation-specific reactions and a control reaction. For the bisulfite-treated samples, the control reaction was a MYOD1 assay as described in Example 1. For the untreated samples, the ACTB primers described for the RT-PCR reactions were used as a control to verify the input of unconverted DNA samples. (The ACTB primers do not span an intron). "No PCR" indicates that no PCR product was obtained on unconverted genomic DNA with COBRA primers designed to amplify bisulfite-converted DNA sequences.

DETAILED DESCRIPTION OF THE INVENTION

Figure 1:
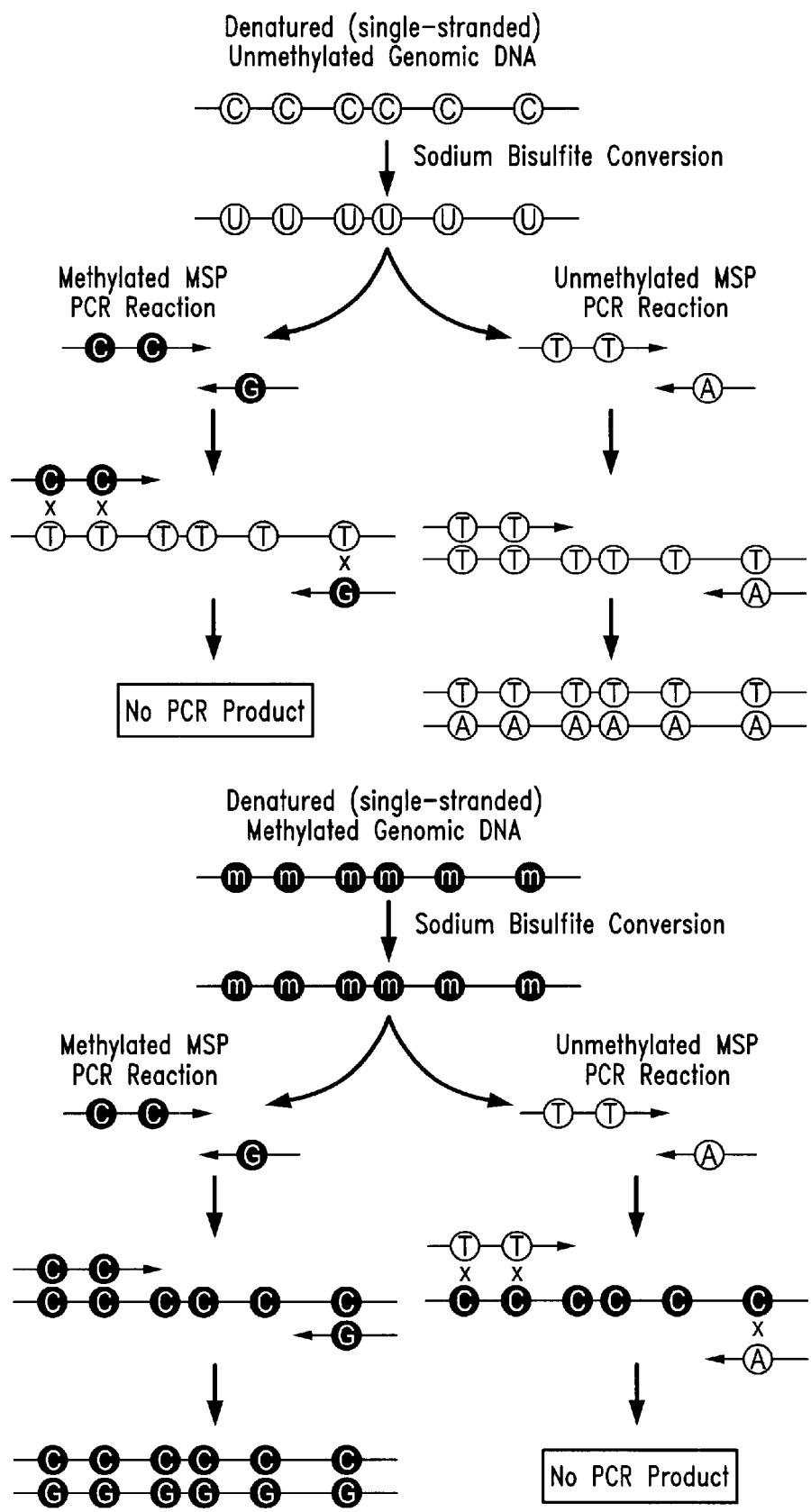
FIG. 1 shows an outline of the MSP technology (prior art) using PCR primers that initially discriminate between methylated and unmethylated (bisulfite-converted) DNA. The top part shows the result of the MSP process when unmethylated single-stranded genomic DNA is initially subjected to sodium bisulfite conversion (deamination of unmethylated cytosine residues to uracil) followed by PCR reactions with the converted template, such that a PCR product appears only with primers specifically annealing to converted (and hence unmethylated) DNA. The bottom portion shows the contrasting result when a methylated single-stranded genomic DNA sample is used. Again, the process first provides for bisulfite treatment followed by PCR reactions such that a PCR product appears only with primers specifically annealing to unconverted (and hence initially methylated) DNA.
Figure 2:
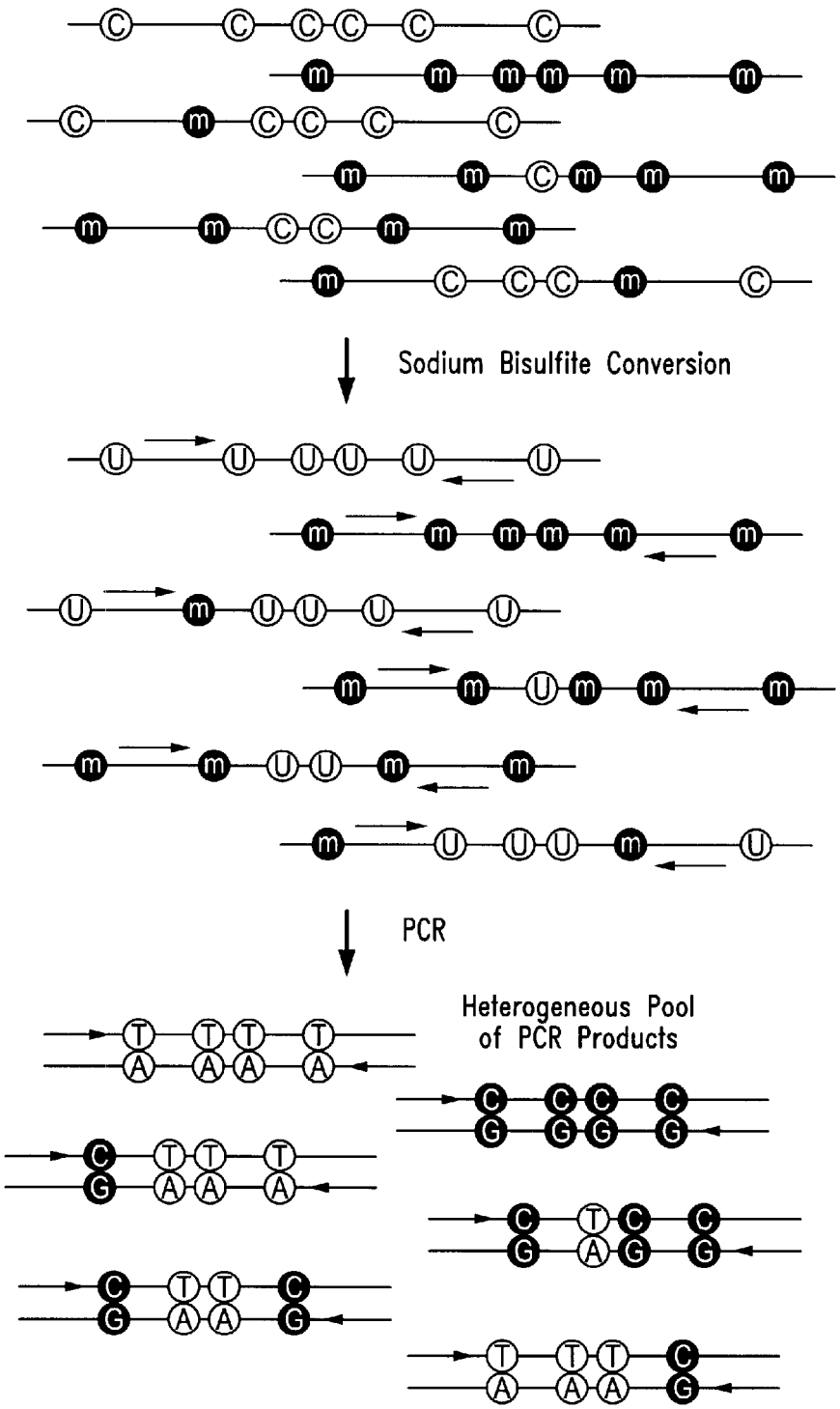
FIG. 2 shows an alternate process for evaluating DNA methylation with sodium bisulfite-treated genomic DNA using nondiscriminating (with respect to methylation status) forward and reverse PCR primers to amplify a specific locus. In this illustration, denatured (i.e., single-stranded) genomic DNA is provided that has mixed methylation status, as would typically be found in a sample for analysis. The sample is converted in a standard sodium bisulfite reaction and the mixed products are amplified by a PCR reaction using primers that do not overlap any CpG dinucleotides. This produces an unbiased (with respect to methylation status) heterogeneous pool of PCR products. The mixed or heterogeneous pool can then be analyzed by a technique capable of detecting sequence differences, including direct DNA sequencing, subcloning of PCR fragments followed by sequencing of representative clones, single-nucleotide primer extension reaction (MS-SNuPE), or restriction enzyme digestion (COBRA).

The present invention provides a rapid, sensitive, reproducible high-throughput method for detecting methylation patterns in samples of nucleic acid. The invention provides for methylation-dependent modification of the nucleic acid, and then uses processes of nucleic acid amplification, detection, or both to distinguish between methylated and unmethylated residues present in the original sample of nucleic acid. In a preferred embodiment, the invention provides for determining the methylation status of CpG islands within samples of genomic DNA.

In contrast to previous methods for determining methylation patterns, detection of the methylated nucleic acid is relatively rapid and is based on amplification-mediated displacement of specific oligonucleotide probes. In a preferred embodiment, amplification and detection, in fact, occur simultaneously as measured by fluorescence-based real-time quantitative PCR ("RT-PCR") using specific, dual-labeled TaqMan® oligonucleotide probes. The displaceable probes can be specifically designed to distinguish between methylated and unmethylated CpG sites present in the original, unmodified nucleic acid sample.

Like the technique of methylation-specific PCR ("MSP"; U.S. Pat. No. 5,786,146), the present invention provides for significant advantages over previous PCR-based and other methods (e.g., Southern analyses) used for determining methylation patterns. The present invention is substantially more sensitive than Southern analysis, and facilitates the detection of a low number (percentage) of methylated alleles in very small nucleic acid samples, as well as paraffin-embedded samples. Moreover, in the case of genomic DNA, analysis is not limited to DNA sequences recognized by methylation-sensitive restriction endonucleases, thus allowing for fine mapping of methylation patterns across broader CpG-rich regions. The present invention also eliminates the any false-positive results, due to incomplete digestion by methylation-sensitive restriction enzymes, inherent in previous PCR-based methylation methods.

The present invention also offers significant advantages over MSP technology. It can be applied as a quantitative process for measuring methylation amounts, and is substantially more rapid. One important advance over MSP technology is that the gel electrophoresis is not only a time-consuming manual task that limits high throughput capabilities, but the manipulation and opening of the PCR reaction tubes increases the chance of sample misidentification and it greatly increases the chance of contaminating future PCR reactions with trace PCR products. The standard method of avoiding PCR contamination by uracil incorporation and the use of Uracil DNA Glycosylase (AmpErase) is incompatible with bisulfite technology, due to the presence of uracil in bisulfite-treated DNA. Therefore, the avoidance of PCR product contamination in a high-throughput application with bisulfite-treated DNA is a greater technical challenge than for the amplification of unmodified DNA. The present invention does not require any post-PCR manipulation or processing. This not only greatly reduces the amount of labor involved in the analysis of bisulfite-treated DNA, but it also provides a means to avoid handling of PCR products that could contaminate future reactions.

Two factors limit MSP to, at best, semi-quantitative applications. First, MSP methylation information is derived from the comparison of two separate PCR reactions (the methylated and the unmethylated versions). There are inherent difficulties in making kinetic comparisons of two different PCR reactions without a highly quantitative method of following the amplification reaction, such as Real-Time Quantitative PCR. The other problem relates to the fact that MSP amplification is provided for by means of particular CpG-specific oligonucleotides; that is, by biased primers. Often, the DNA sequence covered by such primers contains more than one CpG dinucleotide with the consequence that the sequence amplified will represent only one of multiple potential sequence variants present, depending on the DNA methylation pattern in the original genomic DNA. For instance, if the forward primer is a 24-mer oligonucleotide that covers 3 CpGs, then $2^3=8$ different theoretical sequence permutations could arise in the genomic DNA following bisufite conversion within this 24-nucleotide sequence. If only a fully methylated and a fully unmethylated reaction is run, then only 2 out of the 8 possible methylation states are analyzed.

The situation is further complicated if the intermediate methylation states are non-specifically amplified by the fully methylated or fully unmethylated primers. Accordingly, the MSP patent explicitly describes a non-quantitative technique based on the occurrence or non-occurrence of a PCR product in the fully methylated, versus fully unmethylated reaction, rather than a comparison of the kinetics of the two reactions.

By contrast, one embodiment of the present invention provides for the unbiased amplification of all possible methylation states using primers that do not cover any CpG sequences in the original, unmodified DNA sequence. To the extent that all methylation patterns are amplified equally, quantitative information about DNA methylation patterns can then be distilled from the resulting PCR pool by any technique capable of detecting sequence differences (e.g., by fluorescence-based PCR).

Furthermore, the present invention is substantially faster than MSP. As indicated above, MSP relies on the occurrence or non-occurrence of a PCR product in the methylated, versus unmethylated reaction to determine the methylation status of a CpG sequence covered by a primer. Minimally, this requires performing agarose or polyacrylamide gel electrophoretic analysis (see U.S. Pat. No. 5,786,146, FIGS. 2A–2E, and 3A–3E). Moreover, determining the methylation status of any CpG sites within a given MSP amplified region would require additional analyses such as: (a) restriction endonuclease analysis either before, or after (e.g., COBRA analysis; Xiong and Laird, *Nucleic Acids Res.* 25:2532–2534, 1997) nucleic acid modification and amplification, provided that either the unmodified sequence region of interest contains methylation-sensitive sites, or that modification (e.g., bisulfite) results in creating or destroying restriction sites; (b) single nucleotide primer extension reactions (Ms-SNuPE; Gonzalo and Jones, *Nucleic Acids Res* 25: 2529–2531, 1997); or (c) DNA sequencing of the amplification products. Such additional analyses are not only subject to error (incomplete restriction enzyme digestion), but also add substantial time and expense to the process of determining the CpG methylation status of, for example, samples of genomic DNA.

By contrast, in a preferred embodiment of the present invention, amplification and detection occur simultaneously as measured by fluorescence-based real-time quantitative PCR using specific, dual-labeled oligonucleotide probes. In principle, the methylation status at any probe-specific sequence within an amplified region can be determined contemporaneously with amplification, with no requirement for subsequent manipulation or analysis.

As disclosed by MSP inventors, "[t]he only technique that can provide more direct analysis than MSP for most CpG sites within a defined region is genomic sequencing." (U.S. Pat. No. 5,786,146 at 5, line 15–17). The present invention provides, in fact, a method for the partial direct sequencing of modified CpG sites within a known (previously sequenced) region of genomic DNA. Thus, a series of CpG-specific TaqMan® probes, each corresponding to a particular methylation site in a given amplified DNA region, are constructed. This series of probes are then utilized in parallel amplification reactions, using aliquots of a single, modified DNA sample, to simultaneously determine the complete methylation pattern present in the original unmodified sample of genomic DNA. This is accomplished in a fraction of the time and expense required for direct sequencing of the sample of genomic DNA, and are substantially more sensitive. Moreover, one embodiment of the present invention provides for a quantitative assessment of such a methylation pattern.

The present invention has identified four process techniques and associated diagnostic kits, utilizing a methylation-dependent nucleic acid modifying agent (e.g., bisulfite), to both qualitatively and quantitatively determine CpG methylation status in nucleic acid samples (e.g., genomic DNA samples). The four processes are outlined in FIG. 3 and labeled at the bottom with the letters A through D. Overall, methylated-CpG sequence discrimination is designed to occur at the level of amplification, probe hybridization or at both levels. For example, applications C and D utilize "biased" primers that distinguish between modified unmethylated and methylated nucleic acid and provide methylated-CpG sequence discrimination at the PCR amplification level. Process B uses "unbiased" primers (that do not cover CpG methylation sites), to provide for unbiased amplification of modified nucleic acid, but rather utilize probes that distinguish between modified unmethylated and methylated nucleic acid to provide for quantitative methylated-CpG sequence discrimination at the detection level (e.g., at the fluorescent (or luminescent) probe hybridization level only). Process A does not, in itself, provide for methylated-CpG sequence discrimination at either the amplification or detection levels, but supports and validates the other three applications by providing control reactions for input DNA.

Process D. In a first embodiment (FIG. 3, Application D), the invention provides a method for qualitatively detecting a methylated CpG-containing nucleic acid, the method including: contacting a nucleic acid-containing sample with a modifying agent that modifies unmethylated cytosine to produce a converted nucleic acid; amplifying the converted nucleic acid by means of two oligonucleotide primers in the presence of a specific oligonucleotide hybridization probe, wherein both the primers and probe distinguish between modified unmethylated and methylated nucleic acid; and detecting the "methylated" nucleic acid based on amplification-mediated probe displacement.

The term "modifies" as used herein means the conversion of an unmethylated cytosine to another nucleotide by the modifying agent, said conversion distinguishing unmethylated from methylated cytosine in the original nucleic acid sample. Preferably, the agent modifies unmethylated cytosine to uracil. Preferably, the agent used for modifying unmethylated cytosine is sodium bisulfite, however, other equivalent modifying agents that selectively modify unmethylated cytosine, but not methylated cytosine, can be substituted in the method of the invention. Sodium-bisulfite readily reacts with the 5, 6-double bond of cytosine, but not with methylated cytosine, to produce a sulfonated cytosine intermediate that undergoes deamination under alkaline conditions to produce uracil (Example 1). Because Taq polymerase recognizes uracil as thymine and 5-methylcytidine (m5C) as cytidine, the sequential combination of sodium bisulfite treatment and PCR amplification results in the ultimate conversion of unmethylated cytosine residues to thymine (C→U→T) and methylated cytosine residues ("mC") to cytosine (mC→mC→C). Thus, sodium-bisulfite treatment of genomic DNA creates methylation-dependent sequence differences by converting unmethylated cyotsines to uracil, and upon PCR the resultant product contains cytosine only at positions where methylated cytosine occurs in the unmodified nucleic acid.

Oligonucleotide "primers," as used herein, means linear, single-stranded, oligomeric deoxyribonucleic or ribonucleic acid molecules capable of sequence-specific hybridization (annealing) with complementary strands of modified or unmodified nucleic acid. As used herein, the specific primers are preferably DNA. The primers of the invention embrace oligonucleotides of appropriate sequence and sufficient length so as to provide for specific and efficient initiation of polymerization (primer extension) during the amplification process. As used in the inventive processes, oligonucleotide primers typically contain 12–30 nucleotides or more, although may contain fewer nucleotides. Preferably, the primers contain from 18–30 nucleotides. The exact length will depend on multiple factors including temperature (during amplification), buffer, and nucleotide composition. Preferably, primers are single-stranded although double-stranded primers may be used if the strands are first separated. Primers may be prepared using any suitable method, such as conventional phosphotriester and phosphodiester methods or automated embodiments which are commonly known in the art.

As used in the inventive embodiments herein, the specific primers are preferably designed to be substantially complementary to each strand of the genomic locus of interest. Typically, one primer is complementary to the negative (−) strand of the locus (the "lower" strand of a horizontally situated double-stranded DNA molecule) and the other is complementary to the positve (+) strand ("upper" strand). As used in the embodiment of Application D, the primers are preferably designed to overlap potential sites of DNA methylation (CpG nucleotides) and specifically distinguish modified unmethylated from methylated DNA. Preferably, this sequence discrimination is based upon the differential annealing temperatures of perfectly matched, versus mismatched oligonucleotides. In the embodiment of Application D, primers are typically designed to overlap from one to several CpG sequences. Preferably, they are designed to overlap from 1 to 5 CpG sequences, and most preferably from 1 to 4 CpG sequences. By contrast, in a quantitative embodiment of the invention, the primers do not overlap any CpG sequences.

In the case of fully "unmethylated" (complementary to modified unmethylated nucleic acid strands) primer sets, the anti-sense primers contain adenosine residues ("As") in place of guanosine residues ("Gs") in the corresponding (−) strand sequence. These substituted As in the anti-sense primer will be complementary to the uracil and thymidine residues ("Us" and "Ts") in the corresponding (+) strand region resulting from bisulfite modification of unmethylated C residues ("Cs") and subsequent amplification. The sense primers, in this case, are preferably designed to be complementary to anti-sense primer extension products, and contain Ts in place of unmethylated Cs in the corresponding (+) strand sequence. These substituted Ts in the sense primer will be complementary to the As, incorporated in the anti-sense primer extension products at positions complementary to modified Cs (Us) in the original (+) strand.

In the case of fully-methylated primers (complementary to methylated CpG-containing nucleic acid strands), the anti-sense primers will not contain As in place of Gs in the corresponding (−) strand sequence that are complementary to methylated Cs (i.e., mCpG sequences) in the original (+) strand. Similarly, the sense primers in this case will not contain Ts in place of methylated Cs in the corresponding (+) strand mCpG sequences. However, Cs that are not in CpG sequences in regions covered by the fully-methylated primers, and are not methylated, will be represented in the fully-methylated primer set as described above for unmethylated primers.

Preferably, as employed in the embodiment of Application D, the amplification process provides for amplifying bisulfite converted nucleic acid by means of two oligonucleotide primers in the presence of a specific oligonucleotide hybridization probe. Both the primers and probe distinguish between modified unmethylated and methylated nucleic acid. Moreover, detecting the "methylated" nucleic acid is based upon amplification-mediated probe fluorescence. In one embodiment, the fluorescence is generated by probe degradation by 5' to 3' exonuclease activity of the polymerase enzyme. In another embodiment, the fluorescence is generated by fluorescence energy transfer effects between two adjacent hybridizing probes (Lightcycler® technology) or between a hybridizing probe and a primer. In another embodiment, the fluorescence is generated by the primer itself (Sunrise® technology). Preferably, the amplification process is an enzymatic chain reaction that uses the oligonucleotide primers to produce exponential quantities of amplification product, from a target locus, relative to the number of reaction steps involved.

As describe above, one member of a primer set is complementary to the (−) strand, while the other is complementary to the (+) strand. The primers are chosen to bracket the area of interest to be amplified; that is, the "amplicon." Hybridization of the primers to denatured target nucleic acid followed by primer extension with a DNA polymerase and nucleotides, results in synthesis of new nucleic acid strands corresponding to the amplicon. Preferably, the DNA polymerase is Taq polymerase, as commonly used in the art. Although equivalent polymerases with a 5' to 3' nuclease activity can be substituted. Because the new amplicon sequences are also templates for the primers and polymerase, repeated cycles of denaturing, primer annealing, and extension results in exponential production of the amplicon. The product of the chain reaction is a discrete nucleic acid duplex, corresponding to the amplicon sequence, with termini defined by the ends of the specific primers employed. Preferably the amplification method used is that of PCR (Mullis et al., Cold Spring Harb. Symp. Quant. Biol 51:263–273; Gibbs, Anal. Chem. 62:1202–1214, 1990), or more preferably, automated embodiments thereof which are commonly known in the art.

Preferably, methylation-dependent sequence differences are detected by methods based on fluorescence-based quantitative PCR (real-time quantitative PCR, Heid et al., Genome Res. 6:986–994, 1996; Gibson et al., Genome Res. 6:995–1001, 1996) (e.g., "TaqMan®," "Lightcycler®," and "Sunrise®)" technologies). For the TaqMan® and Lightcycler® technologies, the sequence discrimination can occur at either or both of two steps: (1) the amplification step, or (2) the fluorescence detection step. In the case of the "Sunrise®" technology, the amplification and fluorescent steps are the same. In the case of the FRET hybridization, probes format on the Lightcycler®, either or both of the FRET oligonucleotides can be used to distinguish the sequence difference. Most preferably the amplification process, as employed in all inventive embodiments herein, is that of fluorescence-based Real Time Quantitative PCR (Heid et al., Genome Res. 6:986–994, 1996) employing a dual-labeled fluorescent oligonucleotide probe (TaqMan® PCR, using an ABI Prism 7700 Sequence Detection System, Perkin Elmer Applied Biosystems, Foster City, Calif.).

The "TaqMan®" PCR reaction uses a pair of amplification primers along with a nonextendible interrogating oligonucleotide, called a TaqMan® probe, that is designed to hybridize to a GC-rich sequence located between the forward and reverse (i.e., sense and anti-sense) primers. The TaqMan® probe further comprises a fluorescent "reporter moiety" and a "quencher moiety" covalently bound to linker moieties (e.g., phosphoramidites) attached to nucleotides of the TaqMan® oligonucleotide. Examples of suitable reporter and quencher molecules are: the 5' fluorescent reporter dyes 6FAM ("FAM"; 2,7 dimethoxy-4,5-dichloro-6-carboxy-fluorescein), and TET (6-carboxy-4,7,2',7'-tetrachlorofluorescein); and the 3' quencher dye TAMRA (6-carboxytetramethylrhodamine) (Livak et al., PCR Methods Appl. 4:357–362, 1995; Gibson et al., Genome Res. 6:995–1001; and 1996; Heid et al., Genome Res. 6:986–994, 1996).

One process for designing appropriate TaqMan® probes involves utilizing a software facilitating tool, such as "Primer Express" that can determine the variables of CpG island location within GC-rich sequences to provide for at least a 10° C. melting temperature difference (relative to the primer melting temperatures) due to either specific sequence (tighter bonding of GC, relative to AT base pairs), or to primer length.

The TaqMan® probe may or may not cover known CpG methylation sites, depending on the particular inventive process used. Preferably, in the embodiment of Application D, the TaqMan® probe is designed to distinguish between modified unmethylated and methylated nucleic acid by overlapping from 1 to 5 CpG sequences. As described above for the fully unmethylated and fully methylated primer sets, TaqMan® probes may be designed to be complementary to either unmodified nucleic acid, or, by appropriate base substitutions, to bisulfite-modified sequences that were either fully unmethylated or fully methylated in the original, unmodified nucleic acid sample.

Figure 3:
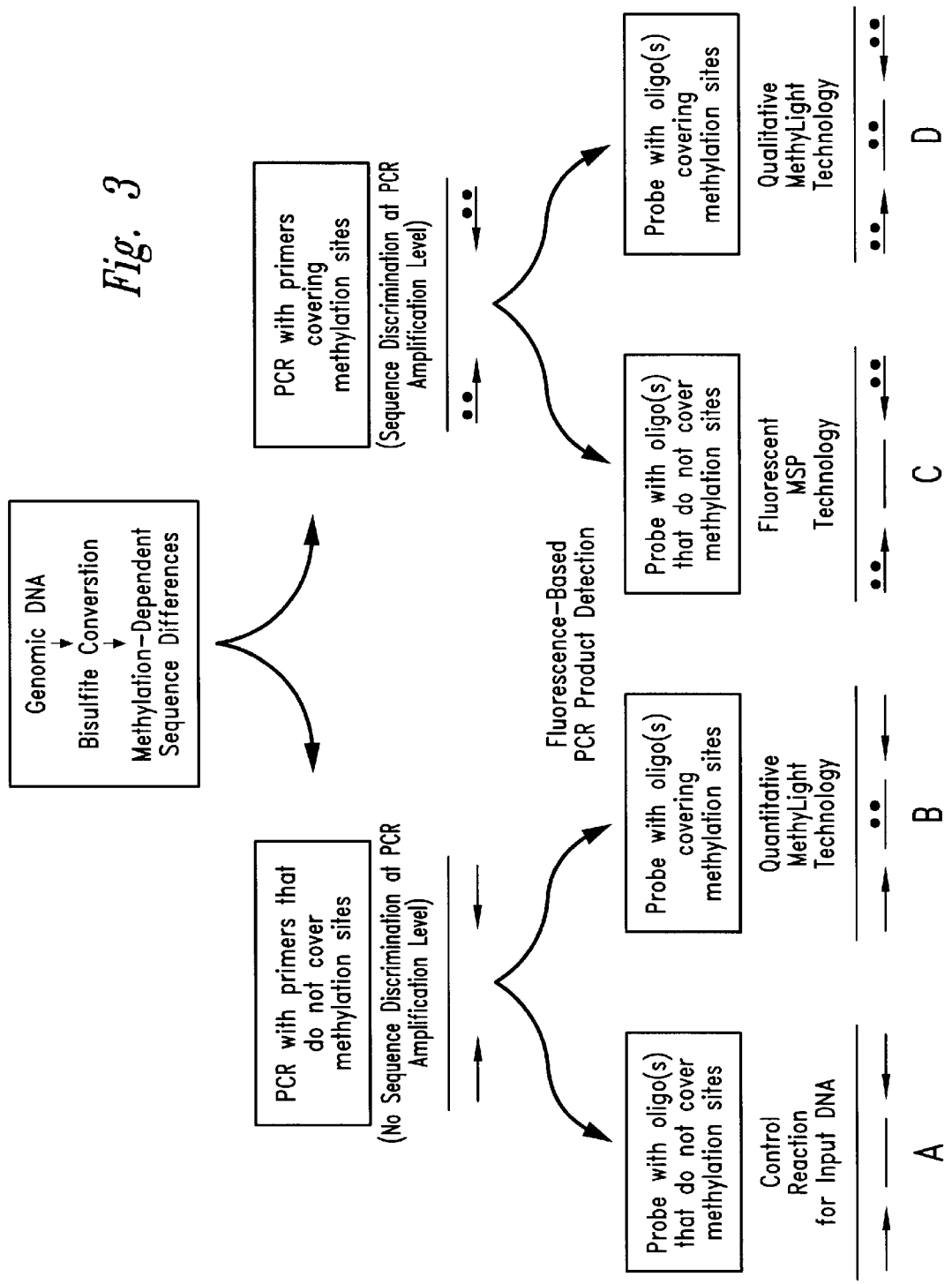
FIGS. 3A–3D shows a flow diagram of the inventive process in several, but not all, alternative embodiments for PCR product analysis. Variations in detection methodology, such as the use of dual probe technology (Lightcycler®) or fluorescent primers (Sunrise® technology) are not shown in this Figure. Specifically, the inventive process begins with a mixed sample of genomic DNA that is converted in a sodium bisulfite reaction to a mixed pool of methylation-dependent sequence differences according to standard procedures (the bisulfite process converts unmethylated cytosine residues to uracil). Fluorescence-based PCR is then performed either in an "unbiased" PCR reaction with primers that do not overlap known CpG methylation sites (left arm of FIG. 3), or in a "biased" reaction with PCR primers that overlap known CpG dinucleotides (right arm of FIG. 3). Sequence discrimination can occur either at the level of the amplification process (C and D) or at the level of the fluorescence detection process (B), or both (D). A quantitative test for methylation patterns in the genomic DNA sample is shown on the left arm (B), wherein sequence discrimination occurs at the level of probe hybridization. In this version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides (A). Alternatively, as shown in the right arm of FIG. 3, a qualitative test for genomic methylation is achieved by probing of the biased PCR pool with either control oligonucleotides that do not "cover" known methylation sites (C; a fluorescence-based version of the MSP technique), or with oligonucleotides covering potential methylation sites (D).
Figure 4:
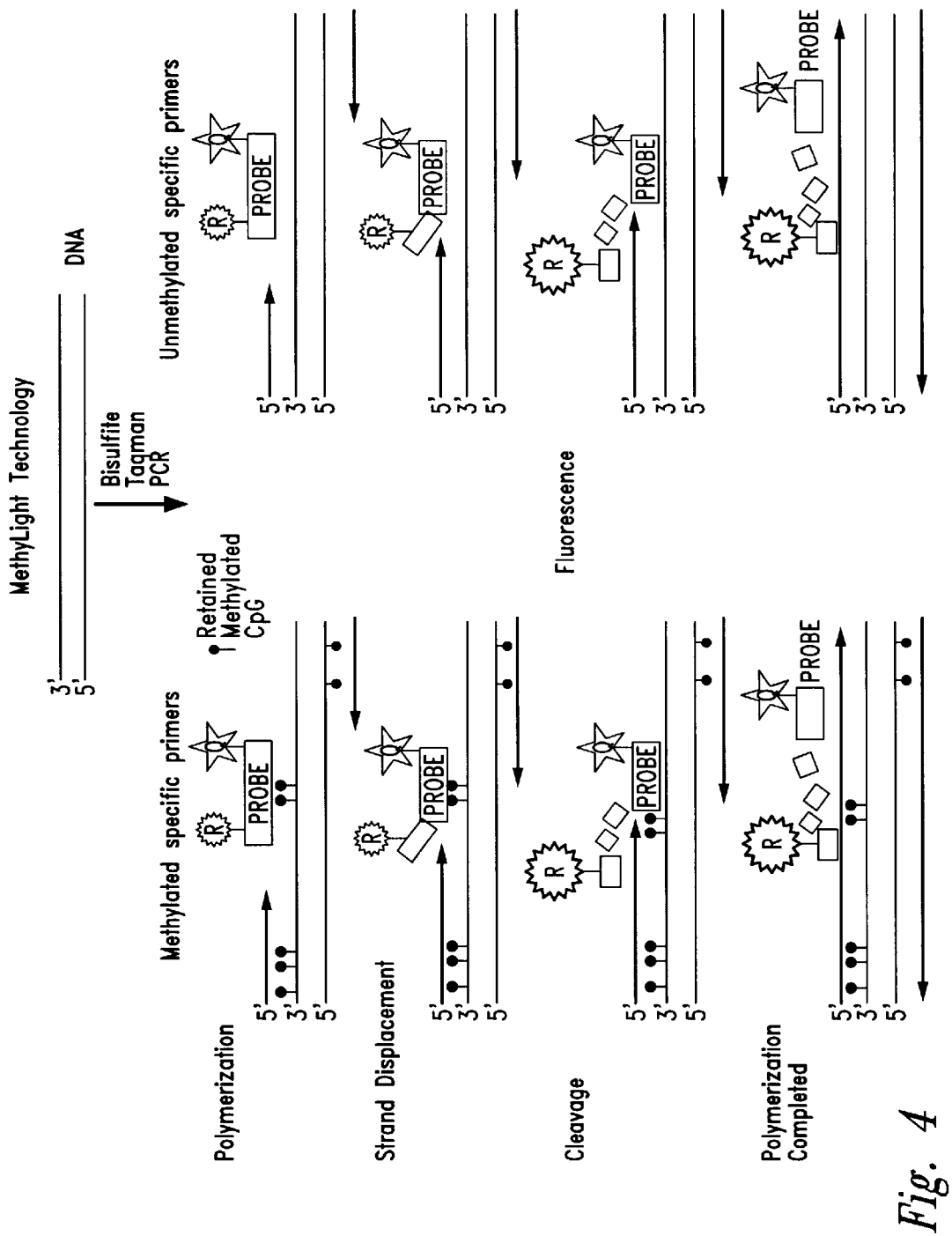
FIG. 4 shows a flow chart overview of the inventive process employing a "TaqMan®" probe in the amplification process. Briefly, double-stranded genomic DNA is treated with sodium bisulfite and subjected to one of two sets of PCR reactions using TaqMan® probes; namely with either biased primers and TaqMan® probe (left column), or unbiased primers and TaqMan® probe (right column). The TaqMan® probe is dual-labeled with a fluorescent "reporter" (labeled "R" in FIG. 4) and "qencher" (labeled "O") molecules, and is designed to be specific for a relatively high GC content region so that it melts out at about 10° C. higher temperature in the PCR cycle than the forward or reverse primers. This allows it to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent system as described herein.

Each oligonucleotide primer or probe in the TaqMan® PCR reaction can span anywhere from zero to many different CpG dinucleotides that each can result in two different sequence variations following bisulfite treatment ($^m$CpG, or UpG). For instance, if an oligonucleotide spans 3 CpG dinucleotides, then the number of possible sequence variants arising in the genomic DNA is $2^3=8$ different sequences. If the forward and reverse primer each span 3 CpGs and the probe oligonucleotide (or both oligonucleotides together in the case of the FRET format) spans another 3, then the total number of sequence permutations becomes 8×8×8=512. In theory, one could design separate PCR reactions to quantitatively analyze the relative amounts of each of these 512 sequence variants. In practice, a substantial amount of qualitative methylation information can be derived from the analysis of a much smaller number of sequence variants. Thus, in its most simple form, the inventive process can be performed by designing reactions for the fully methylated and the fully unmethylated variants that represent the most extreme sequence variants in a hypothetical example (see FIG. 3, Application D). The ratio between these two reactions, or alternatively the ratio between the methylated reaction and a control reaction (FIG. 3, Application A), would provide a measure for the level of DNA methylation at this locus. A more detailed overview of the qualitative version is shown in FIG. 4.

Detection of methylation in the embodiment of Application D, as in other embodiments herein, is based on amplification-mediated displacement of the probe. In theory, the process of probe displacement might be designed to leave the probe intact, or to result in probe digestion. Preferably, as used herein, displacement of the probe occurs by digestion of the probe during amplification. During the extension phase of the PCR cycle, the fluorescent hybridization probe is cleaved by the 5' to 3' nucleolytic activity of the DNA polymerase. On cleavage of the probe, the reporter moiety emission is no longer transferred efficiently to the quenching moiety, resulting in an increase of the reporter moiety fluorescent-emission spectrum at 518 nm. The fluorescent intensity of the quenching moiety (e.g., TAMRA), changes very little over the course of the PCR amplification. Several factors my influence the efficiency of TaqMan® PCR reactions including: magnesium and salt concentrations; reaction conditions (time and temperature); primer sequences; and PCR target size (i.e., amplicon size) and composition. Optimization of these factors to produce the optimum fluorescence intensity for a given genomic locus is obvious to one skilled in the art of PCR, and preferred conditions are further illustrated in the "Examples" herein. The amplicon may range in size from 50 to 8,000 base pairs, or larger, but may be smaller. Typically, the amplicon is from 100 to 1000 base pairs, and preferably is from 100 to 500 base pairs. Preferably, the reactions are monitored in real time by performing PCR amplification using 96-well optical trays and caps, and using a sequence detector (ABI Prism) to allow measurement of the fluorescent spectra of all 96 wells of the thermal cycler continuously during the PCR amplification. Preferably, process D is run in combination with the process A (FIG. 3) to provide controls for the amount of input nucleic acid, and to normalize data from tray to tray.

Application C. The inventive process can be modified to avoid sequence discrimination at the PCR product detection level. Thus, in an additional qualitative process embodiment (FIG. 3, Application C), just the primers are designed to cover CpG dinucleotides, and sequence discrimination occurs solely at the level of amplification. Preferably, the probe used in this embodiment is still a TaqMan® probe, but is designed so as not to overlap any CpG sequences present in the original, unmodified nucleic acid. The embodiment of Application C represents a high-throughput, fluorescence-based real-time version of MSP technology, wherein a substantial improvement has been attained by reducing the time required for detection of methylated CpG sequences. Preferably, the reactions are monitored in real time by performing PCR amplification using 96-well optical trays and caps, and using a sequence detector (ABI Prism) to allow measurement of the fluorescent spectra of all 96 wells of the thermal cylcer continuously during the PCR amplification. Preferably, process C is run in combination with process A to provide controls for the amount of input nucleic acid, and to normalize data from tray to tray.

Application B. The inventive process can be also be modified to avoid sequence discrimination at the PCR amplification level (FIG. 3, A and B). In a quantitative process embodiment (FIG. 3, Application B), just the probe is designed to cover CpG dinucleotides, and sequence discrimination occurs solely at the level of probe hybridization. Preferably, TaqMan® probes are used. In this version, sequence variants resulting from the bisulfite conversion step are amplified with equal efficiency; as long as there is no inherent amplification bias (Warnecke et al., *Nucleic Acids Res.* 25:4422–4426, 1997). Design of separate probes for each of the different sequence variants associated with a particular methylation pattern (e.g., $2^3=8$ probes in the case of 3 CpGs) would allow a quantitative determination of the relative prevalence of each sequence permutation in the mixed pool of PCR products. Preferably, the reactions are monitored in real time by performing PCR amplification using 96-well optical trays and caps, and using a sequence detector (ABI Prism) to allow measurement of the fluorescent spectra of all 96 wells of the thermal cylcer continuously during the PCR amplification. Preferably, process B is run in combination with process A to provide controls for the amount of input nucleic acid, and to normalize data from tray to tray.

Application A. Process A (FIG. 3) does not, in itself, provide for methylated-CpG sequence discrimination at either the amplification or detection levels, but supports and validates the other three applications by providing control reactions for the amount of input DNA, and to normalize data from tray to tray. Thus, if neither the primers, nor the probe overlie any CpG dinucleotides, then the reaction represents unbiased amplification and measurement of amplification using fluorescent-based quantitative real-time PCR serves as a control for the amount of input DNA (FIG. 3, Application A). Preferably, process A not only lacks CpG dinucleotides in the primers and probe(s), but also does not contain any CpGs within the amplicon at all to avoid any differential effects of the bisulfite treatment on the amplification process. Preferably, the amplicon for process A is a region of DNA that is not frequently subject to copy number alterations, such as gene amplification or deletion.

Results obtained with the qualitative version of the technology are described in the examples below. Dozens of human tumor samples have been analyzed using this technology with excellent results. High-throughput using a Taq-Man® machine allowed performance of 1100 analyses in three days with one TaqMan® machine.

EXAMPLE 1

An initial experiment was performed to validate the inventive strategy for assessment of the methylation status of CpG islands in genomic DNA. This example shows a comparison between human sperm DNA (known to be highly unmethylated) and HCT116 DNA (from a human colorectal cell line, known to be highly methylated at many CpG sites) with respect to the methylation status of specific, hypermethylatable CpG islands in four different genes. COBRA (combined bisulfite restriction analysis; Xiong and Laird, *Nucleic Acids Res.* 25:2532–2534, 1997) was used as an independent measure of methylation status.

DNA Isolation and Bisulfite Treatment. Briefly, genomic DNA was isolated from human sperm or HCT116 cells by the standard method of proteinase K digestion and phenol-chloroform extraction (Wolf et al., *Am. J Hum. Genet.* 51:478–485, 1992). The DNA was then treated with sodium bisulfite by initially denaturing in 0.2 M NaOH, followed by addition of sodium bisulfite and hydroquinone (to final concentrations of 3.1 M, and 0.5M, respectively), incubation for 16 h. at 55° C., desalting (DNA Clean-Up System; Promega), desulfonation by 0.3M NaOH, and final ethanol precipitation. (Xiong and Laird, supra, citing Sadri and Hornsby, *Nucleic Acids Res.* 24:5058–5059, 1996; see also Frommer et al, *Proc. Natl Acad. Sci. USA* 89:1827–1831, 1992). After bisulfite treatment, the DNA was subjected either to COBRA analysis as previously described (Xiong and Laird, supra), or to the inventive amplification process using fluorescence-based, real-time quantitative PCR (Heid et al., *Genome Res.* 6:986–994, 1996; Gibson et al., *Genome Res.* 6:995–1001, 1996).

COBRA and MsSNuPE reactions. ESR1 and APC genes were analyzed using COBRA (Combined Bisulfite Restriction Analysis). For COBRA analysis, methylation-dependent sequence differences were introduced into the genomic DNA by standard bisulfite treatment according to the procedure described by Frommer et al (*Proc. Natl. Acad. Sci. USA* 89:1827–1831, 1992) (1 ug of salmon sperm DNA was added as a carrier before the genomic DNA was treated with sodium bisulfite). PCR amplification of the bisulfite converted DNA was performed using primers specific for the interested CpG islands, followed by restriction endonuclease digestion, gel electrophoresis, and detection using specific, labeled hybridization probes. The forward and reverse primer sets used for the ESR1 and APC genes are: TCCTAAAACTACACTTACTCC [SEQ ID NO. 35], GGT-TATTTGGAAAAAGAGTATAG [SEQ ID NO. 36] (ESR1 promoter); and AGAGAGAAGTAGTTGTGTTAAT [SEQ ID NO. 37], ACTACACCAATACAACCACAT [SEQ ID NO. 38] (APC promoter), respectively. PCR products of ESR1 were digested by restriction endonucleases TaqI and BstUI, while the products from APC were digested by Taq I and SfaN I, to measure methylation of 3 CpG sies for APC and 4 CpG sites for ESR1. The digested PCR products were electrophoresed on denaturing polyacrylamide gel and transferred to nylon membrane (Zetabind; American Bioanalytical) by electroblotting. The membranes were hybridized by a 5'-end labeled oligonucleotide to visualize both digested and undigested DNA fragments of interest. The probes used are as follows: ESR1, AAACCAAAACTC [SEQ ID NO. 39]; and APC, CCCACACCCAACCAAT [SEQ ID NO. 40]. Quantitation was performed with the Phosphoimager 445SI (Molecular Dynamics). Calculations were performed in Microsoft Excel. The level of DNA methylation at the investigated CpG sites was determined by calculating the percentage of the digested PCR fragments (Xiong and Laird, supra).

MLH1 and CDKN2A were analyzed using MsSNuPE (Methylation-sensitive Single Nucleotide Primer Extension Assay), performed as decribed by Gonzalgo and Jones (*Nucleic Acids Res.* 25:2529–2531). PCR amplification of the bisulfite converted DNA was performed using primers specific for the interested CpG islands, and detection was performed using additional specific primers (extension probes). The forward and reverse primer sets used for the MLH1 and CDKN2A genes are: GGAGGTTATAAGAG-TAGGGTTAA [SEQ ID NO. 41], CCAACCAATAAAAA-CAAAAATACC [SEQ ID NO. 42] (MLH1 promoter); GTAGGTGGGGAGGAGTTTAGTT [SEQ ID NO.43], TCTAATAACCAACCAACCCCTCC [SEQ ID NO. 44] (CDKN2A promoter); and TTGTAT-TATTTTGTTTTTTTGGTAGG [SEQ ID NO.45], CAACTTCTCAAATCATCAATCCTCAC [SEQ ID NO. 46] (CDKN2A Exon 2), respectively. The MsSNuPE extension probes are located immediately 5' of the CpG to be analyzed, and the sequences are: TTTAGTAGAGG-TATATAAGTT [SEQ ID NO. 47], TAAGGGGAGAGGAG-GAGTTTGAGAAG [SEQ ID NO. 48] (MLH1 promoter sites 1 and 2, respectively); TTTGAGGGATAGGGT [SEQ ID NO. 49], TTTTAGGGGTGTTATATT [SEQ ID NO. 50], TTTTTTTGTTTGGAAAGATAT [SEQ ID NO. 51] (promoter sites 1, 2, and 3, respectively); and GTTGGTG-GTGTTGTAT [SEQ ID NO. 52], AGGTTATGAT-GATGGGTAG [SEQ ID NO. 53], TATTAGAGGTAG-TAATTATGTT [SEQ ID NO. 54] (Exon2 sites 1, 2, and 3, respectively). A pair of reactions was set up for each sample using either 32p-dCTP or 32p-dTTP for single nucleotide extension. The extended MsSNuPE primers (probes) were separated by denaturing polyacrylamide gel. Quantitation was performed using the Phosphoimager.

Inventive methylation analysis. Bisulfite-converted genomic DNA was amplified using locus-specific PCR primers flanking an oligonucleotide probe with a 5' fluorescent reporter dye (6FAM) and a 3' quencher dye (TAMRA) (Livak et al., *PCR Methods Appl.* 4:357–362, 1995) (primers and probes used for the methylation analyses are listed under "Genes, MethyLight Primers and Probe Sequences" herein, infra). In this example, the forward and reverse primers and the corresponding fluorogenic probes were designed to discriminate between either fully methylated or fully unmethylated molecules of bisulfite-converted DNA (see discussion of primer design under "Detailed Description of the Invention, Process D" herein). Primers and a probe were also designed for a stretch of the MYOD1 gene (Myogenic Differentiation Gene), completely devoid of CpG dinucleotides as a control reaction for the amount of input DNA. Parallel reactions were performed using the inventive process with the methylated and unmethylated (D), or control oligos (A) on the bisulfite-treated sperm and HCT116 DNA samples. The values obtained for the methylated and unmethylated reactions were normalized to the values for the MYOD1 control reactions to give the ratios shown in Table 1 (below).

In a TaqMan® protocol, the 5' to 3' nuclease activity of Taq DNA polymerase cleaved the probe and released the reporter, whose fluorescence was detected by the laser detector of the ABI Prism 7700 Sequence Detection System (Perkin-Elmer, Foster City, Calif.). After crossing a fluorescence detection threshold, the PCR amplification resulted in a fluorescent signal 25' proportional to the amount of PCR product generated. Initial template quantity can be derived from the cycle number at which the fluorescent signal crosses a threshold in the exponential phase of the PCR reaction. Several reference samples were included on each assay plate to verify plate-to-plate consistency. Plates were normalized to each other using these reference samples. The PCR amplification was performed using a 96-well optical tray and caps with a final reaction mixture of 25 $\mu$l consisting of 600 nM each primer, 200 nM probe, 200 $\mu$M each dATP, dCTP, dGTP, 400 $\mu$M dUTP, 5.5 mM MgCl$_2$, 1×TaqMan® Buffer A containing a reference dye, and bisulfite-converted DNA or unconverted DNA at the following conditions: 50° C. for 2 min, 95° C. for 10 min, followed by 40 cycles at 95° C. for 15 s and 60° C. for 1 min.

Genes, MethyLight Primers and Probe Sequences. Four human genes were chosen for analysis: (1) APC (adenomatous polyposis coli) (Hiltunen et al., *Int. J Cancer* 70:644–648, 1997); (2) ESR1 (estrogen receptor) (Issa et al.,

*Nature Genet.* 7:53640, 1994); (3) CDKN2A (p16) (Ahuja, *Cancer Res.* 57:3370–3374, 1997); and (4) hMLH1 (mismatch repair) (Herman et al., *Proc. Natl. Acad. Sci. USA*. 95:6870–6875, 1998; Veigl et al., *Proc. Natl. Acad. Sci. USA*. 95:8698–8702, 1998). These genes were chosen because they contain hypermethylatable CpG islands that are known to undergo de novo methylation in human colorectal tissue in all normal and tumor samples. The human APC gene, for example, has been linked to the development of colorectal cancer, and CpG sites in the regulatory sequences of the gene are known to be distinctly more methylated in colon carcinomas, but not in premalignant adenomas; relative to normal colonic mucosa (Hiltunen et al., supra). The human ESR gene contains a CpG island at its 5' end, which becomes increasingly methylated in colorectal mucosa with age and is heavily methylated in all human colorectal tumors analyzed (Issa et al., supra). Hypermethylation of promoter-associated CpG islands of the CDKN2A (p16) gene has been found in 60% of colorectal cancers showing microsatellite instability (MI) due to defects in one of several base mismatch repair genes (Ahuja et al., supra). The mismatch repair gene MLH1 plays a pivotal role in the development of sporadic cases of mismatch repair-deficient colorectal tumors (Thibodeau et al., *Science* 260:816–819, 1993). It has been reported that MLH1 can become transcriptionally silenced by DNA hypermethylation of its promoter region, leading to microsatellite instability (MSI) (Kane et al., *Cancer Res.* 57:808–811, 1997; Ahuja et al., supra; Cunningham et al., *Cancer Res.* 58:3455–3460, 1998; Herman et al., supra; Veigl et al., supra).

Five sets of PCR primers and probes, designed specifically for bisulfite converted DNA sequences, were used: (1) a set representing fully methylated and fully unmethylated DNA for the ESR1 gene; (2) a fully methylated set for the MLH1 gene; (3) a fully methylated and fully unmethylated set for the APC gene; and (4) a fully methylated and fully unmethylated set for the CDKN2A (p16) gene; and (5) an internal reference set for the MYOD1 gene to control for input DNA. The methylated and unmethylated primers and corresponding probes were designed to overlap 1 to 5 potential CpG dinucleotides sites. The MYOD1 internal reference primers and probe were designed to cover a region of the MYOD1 gene completely devoid of any CpG dinucleotides to allow for unbiased PCR amplification of the genomic DNA, regardless of methylation status. As indicated above, parallel TaqMan® PCR reactions were performed with primers specific for the bisulfite-converted methylated and/or unmethylated gene sequences and with the MYOD1 reference primers. The primer and probe sequences are listed below. In all cases, the first primer listed is the forward PCR primer, the second is the TaqMan® probe, and the third is the reverse PCR primer. ESR1 methylated (GGCGTTCGTTTTGGGATTG [SEQ ID NO. 1], 6FAM 5'-CGATAAAACCGAACGACCCGACGA-3' TAMRA [SEQ ID NO. 2], GCCGACACGCGAACTCTAA [SEQ ID NO. 3]); ESR1 unmethylated (ACACATATCCCACCAACACACAA [SEQ ID NO. 4], 6FAM 5'-CAACCCTACCCCAAAAACCTACAAATCCAA-3'TAMRA [SEQ ID NO. 5], AGGAGTTGGTGGAGGGTGTTT [SEQ ID NO. 6]); MLH1 methylated (CTATCGCCGCCTCATCGT [SEQ ID NO. 7], 6FAM 5'-CGCGACGTCAAACGCCACTACG-3' TAMRA [SEQ ID NO. 8], CGTTATATATCGTTCGTAGTATTCGTGTTT [SEQ ID NO. 9]); APC methylated (TTATATGTCGGTTACGTGCGTTTATAT [SEQ ID NO. 10], 6FAM 5'-CCCGTCGAAAACCCGCCGATTA-3' TAMRA [SEQ ID NO. 11], GAACCAAAACGCTCCCCAT [SEQ ID NO. 12]); APC unmethylated (GGGTTGTGAGGGTATATTTTTGAGG [SEQ ID NO. 13], 6FAM 5'-CCCACCCAACCACACAACCTACCTAACC-3' TAMRA [SEQ ID NO. 14], CCAACCCACACTCCACAATAAA [SEQ ID NO. 15]); CDKN2A methylated (AACAACGTCCGCACCTCCT [SEQ ID NO. 16], 6FAM 5'-ACCCGACCCCGAACCGCG-3' TAMRA [SEQ ID NO. 17], TGGAATTTTCGGTTGATTGGTT [SEQ ID NO. 18]); CDKN2A unmethylated (CAACCAATCAACCAAAAATTCCAT [SEQ ID NO. 19], 6FAM 5'-CCACCACCCACTATCTACTCTCCCCCTC-3' TAMRA [SEQ ID NO. 20], GGTGGATTGTGTGTGTTTGGTG [SEQ ID NO. 21]); and MYOD1, (CCAACTCCAAATCCCCTCTCTAT [SEQ ID NO. 22], 6FAM 5'-TCCCTTCCTATTCCTAAATCCAACCTAAATAC CTCC-3' TAMRA [SEQ ID NO. 23], TGATTAATTTAGATTGGGTTTAGAGAAGGA [SEQ ID NO. 24]).

Tables 1 and 2 shows the results of the analysis of human sperm and HCT116 DNAs for methylation status of the CpG islands within the four genes; APC, ESR1, CDKN2A (p16), and hMLH1. The results are expressed as ratios between the methylated and unmethylated reactions and a control reaction (MYOD1). Table 1 shows that sperm DNA yielded a positive ratio only with the "unmethylated" primers and probe; consistent with the known unmethylated status of sperm DNA, and consistent with the percent methylation values determined by COBRA analysis. That is, priming on the bisulfite-treated DNA occurred from regions that contained unmethylated cytosine in CpG sequences in the corresponding genomic DNA, and hence were deaminated converted to uracil) by bisulfite treatment.

TABLE 1

| Technique | COBRA or Ms-SNuPE | Methylated Reaction* | Unmethylated Reaction* |
| --- | --- | --- | --- |
| GENE | | | |
| APC | 0% | 0 | 49 |
| ESR1 | 0% | 0 | 62 |
| CDKN2A | 0%** | 0 | 52 |
| hMLH1 | ND | 0 | ND |

*The values do not represent percentages, but values in an arbitrary unit that can be compared quantitatively between different DNA samples for the same reaction, after normalization with a control gene.
**Based on Ms-SNuPE.

Table 2 shows the results of an analysis of HCT116 DNA for methylation status of the CpG islands within the four genes; APC, ESR1, CDKN2A (p16), and hMLH1. The results are expressed as ratios between the methylation-specific reactions and a control reaction (MYOD1). For the ESR gene, a positive ratio was obtained only with the "methylated" primers and probe; consistent with the known methylated status of HCT116 DNA, and the COBRA analysis. For the CDKN2A gene, HCT116 DNA yielded positive ratios with both the "methylated" and "unmethylated" primers and probe; consistent with the known methylated status of HCT116 DNA, and with the COBRA analysis that indicates only partial methylation of this region of the gene. By contrast, the APC gene gave positive results only with the unmethylated reaction. However, this is entirely consistent with the COBRA analysis, and indicates that this APC gene region is unmethylated in HCT116 DNA. This may indicate that the methylation state of this particular APC gene regulatory region in the DNA from the HCT116 cell line is more like that of normal colonic mucosa or premalignant adenomas rather than that of colon carcinomas (known to be distinctly more methylated).

TABLE 2

| Technique | COBRA and/or Ms-SNuPE | Methylated Reaction* | Unmethylated Reaction* |
|---|---|---|---|
| GENE | | | |
| APC | 2% | 0 | 81 |
| ESR1 | 99% | 36 | 0 |
| CDKN2A | 38%** | 222 | 26 |
| hMLH1 | ND | 0 | ND |

*The values do not represent percentages, but values in an arbitrary unit that can be compared quantitatively between different DNA samples for the same reaction, after normalization with a control gene.
** Based on Ms-SNuPE.

EXAMPLE 2

Figure 5A:
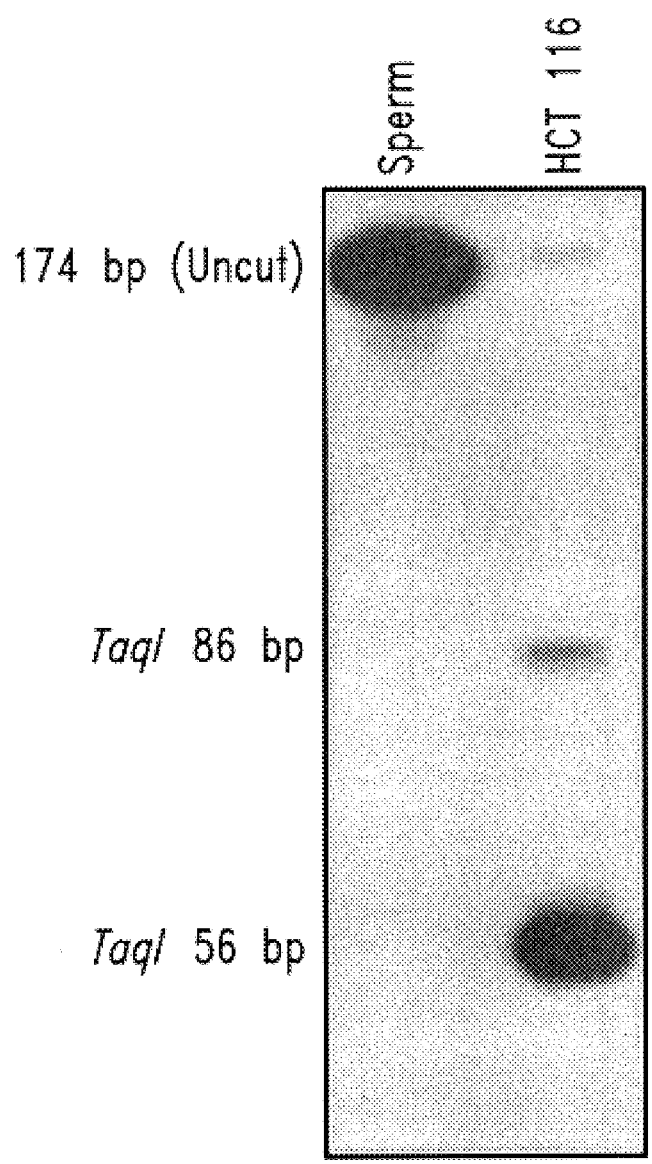

This example is a comparison of the inventive process (A and D in FIG. 3) with an independent COBRA method (See "Methods," above) to determine the methylation status of a CpG island associated with the estrogen receptor (ESR1) gene in the human colorectal cell line HCT116 and in human sperm DNA. This CpG island has been reported to be highly methylated in HCT116 and unmethylated in human sperm DNA (Xiong and Laird, supra; Issa et al., supra). The COBRA analysis, is described above. Two TaqI sites within this CpG island confirmed this, showing a lack of methylation in the sperm DNA and nearly complete methylation in HCT116 DNA (FIG. 5A). Additionally, results using bisulfite-treated and untreated DNA were compared.

For an analysis, fully "methylated" and fully "unmethylated" ESR1, and control MYOD1 primers and probes were designed as described above under "Example 1." Three separate reactions using either the "methylated," "unmethylated" or control oligos on both sperm and HCT116 DNA were performed. As in Example 1, above, the values obtained for the methylated and unmethylated reactions were normalized to the values for the MYOD1 control reactions to give the ratios shown in FIG. 5B. Sperm DNA yielded a positive ratio only with the unmethylated primers and probe, consistent with its unmethylated status. In contrast, HCT116 DNA, with predominantly methylated ESR1 alleles, generated a positive ratio only in the methylated reaction (FIG. 5B). Both the sperm and HCT116 DNA yielded positive values in the MYOD1 reactions, indicating that there was sufficient input DNA for each sample. As expected, the non-bisulfite converted DNA with either the methylated or unmethylated oligonucleotides (FIG. 5B) was not amplified. These results are consistent with the COBRA findings (FIG. 5A), suggesting that the inventive assay can discriminate between the methylated and unmethylated alleles of the ESR1 gene. In addition, the reactions are specific to bisulfite-converted DNA, which precludes the generation of false positive results due to incomplete bisulfite conversion.

EXAMPLE 3

Figure 6A:
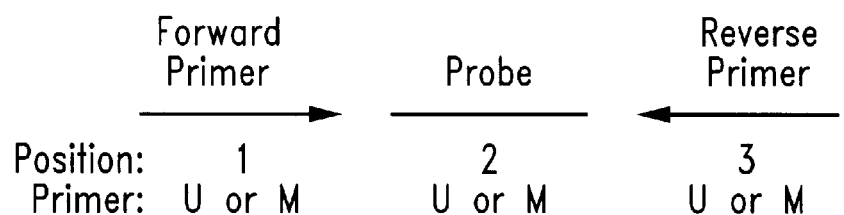
FIG. 6A–6C illustrates a determination of the specificity of the oligonucleotides. Eight different combinations of forward primer, probe and reverse primer were tested on DNA samples with known methylation or lack of methylation at the ESR1 locus. Panel A shows the nomenclature used for the combinations of the ESR1 oligos. "U" refers to the oligo sequence that anneals with bisulfite-converted unmethylated DNA, while "M" refers to the methylated version. Position 1 indicates the forward PCR primer, position 2 the probe, and position 3 the reverse primer. The combinations used for the eight reactions are shown below each pair of bars, representing duplicate experiments. The results are expressed as ratios between the ESR1 values and the MYOD1 control values. Panel B represents an analysis of human sperm DNA. Panel C represents an analysis of DNA obtained from the human colorectal cancer cell line HCT116.
Figure 6B:
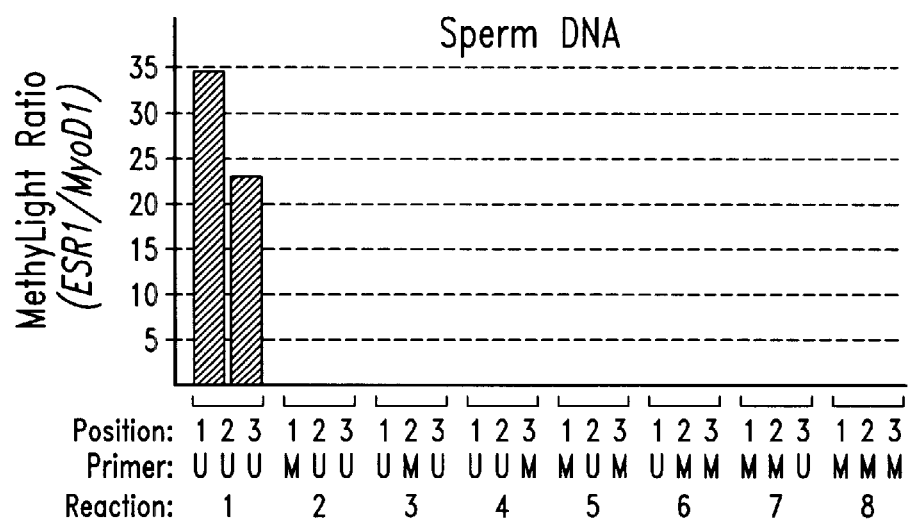
Figure 6C:
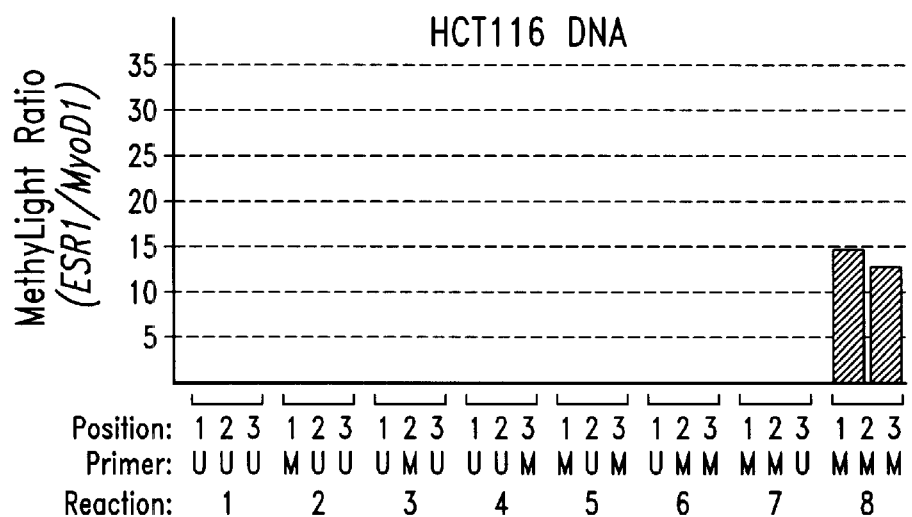

This example determined specificity of the inventive primers and probes. FIG. 6 shows a test of all possible combinations of primers and probes to further examine the specificity of the methylated and unmethylated oligonucleotides on DNAs of known methylation status. Eight different combinations of the ESR1 "methylated" and "unmethylated" forward and reverse primers and probe (as described above in "Example 1") were tested in different combinations in inventive assays on sperm and HCT 116 DNA in duplicate. The assays were performed as described above in Example 1. Panel A (FIG. 6) shows the nomenclature used for the combinations of the ESR1 oligos. "U" refers to the oligo sequence that anneals with bisulfite-converted unmethylated DNA, while "M" refers to the methylated version. Position 1 indicates the forward PCR primer, position 2 the probe, and position 3 the reverse primer. The combinations used for the eight reactions are shown below each pair of bars, representing duplicate experiments. The results are expressed as ratios between the ESR1 values and the MYOD1 control values. Panel B represents an analysis of human sperm DNA. Panel C represents an analysis of DNA obtained from the human colorectal cancer cell line HCT116.

Only the fully unmethylated (reaction 1) or fully methylated combinations (reaction 8) resulted in a positive reaction for the sperm and HCT116, respectively. The other combinations were negative, indicating that the PCR conditions do not allow for weak annealing of the mismatched oligonucleotides. This selectivity indicates that the inventive process can discriminate between fully methylated or unmethylated alleles with a high degree of specificity.

EXAMPLE 4

Figure 7:
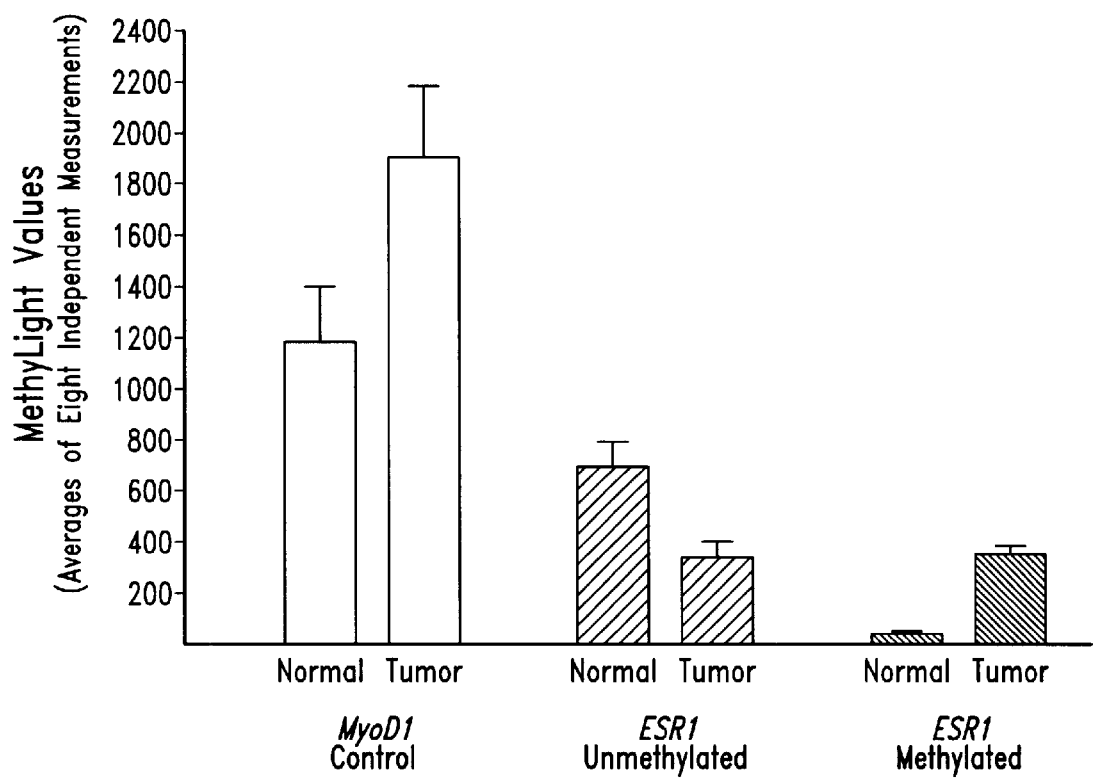
FIG. 7 shows a test of the reproducibility of the reactions. Assays were performed in eight independent reactions to determine the reproducibility on samples of complex origin. A primary human colorectal adenocarcinoma and matched normal mucosa was used for this purpose (samples 10N and 10T shown in FIG. 8). The results shown in this figure represent the raw values obtained in the assay. The values have been plate-normalized, but not corrected for input DNA. The bars indicate the mean values obtained for the eight separate reactions. The error bars represent the standard error of the mean.

This example shows that the inventive process is reproducible. FIG. 7 illustrates an analysis of the methylation status of the ESR1 locus in DNA samples derived from a primary colorectal adenocarcinoma and matched normal mucosa derived from the same patient (samples 10N and 10T in FIG. 8) in order to study a heterogeneous population of methylated and unmethylated alleles. The colorectal tissue samples were collected as described in Example 5, below. In addition, the reproducibility of the inventive process was tested by performing eight independent reactions for each assay. The results for the ESR1 reactions and for the MYOD1 control reaction represent raw absolute values obtained for these reactions, rather than ratios, so that the standard errors of the individual reactions can be evaluated. The values have been plate-normalized, but not corrected for input DNA. The bars indicate the mean values obtained for the eight separate reactions. The error bars represent the standard error of the mean.

FIG. 7 shows that the mean value for the methylated reaction was higher in the tumor compared to the normal tissue whereas the unmethylated reaction showed the opposite result. The standard errors observed for the eight independent measurements were relatively modest and were comparable to those reported for other studies utilizing TaqMan® technology (Fink et al., Nature Med. 4:1329–1333, 1998). Some of the variability of the inventive process may have been a result of stochastic PCR amplification (PCR bias), which can occur at low template concentrations. (Warnecke et al., Nucleic Acids Res. 25:4422–4426,1997). In summary, these results indicate that the inventive process can yield reproducible results for complex, heterogeneous DNA samples.

EXAMPLE 5

This example shows a comparison of MLH1 Expression, microsatellite instability and MLH1 promoter methylation in 25 matched-paired human colorectal samples. The main benefit of the inventive process is the ability to rapidly screen human tumors for the methylation state of a particular locus. In addition, the analysis of DNA methylation as a surrogate marker for gene expression is a novel way to obtain clinically useful information about tumors. We tested the utility of the inventive process by interrogating the methylation status of the MLH1 promoter. The mismatch repair gene MLH1 plays a pivotal role in the development of sporadic cases of mismatch repair-deficient colorectal tumors (Thibodeau et al., *Science* 260:816–819, 1993). It has been reported that MLH1 can become transcriptionally silenced by DNA hypermethylation of its promoter region, leading to microsatellite instability (MSI) (Kane et al., *Cancer Res* 57:808–811, 1997; Ahuja et al., *Cancer Res* 57:3370–3374, 1997; Cunningham et al., *Cancer Res.* 58:3455–3460, 1998; Herman, J. G. et al., *Proc. Natl. Acad. Sci. USA* 95:6870–6875, 1998; Veigl et al., *Proc. Natl. Acad. Sci. USA* 95:8698–8702, 1998).

Using the high-throughput inventive process, as described in Example 1 Application D, 50 samples consisting of 25 matched pairs of human colorectal adenocarcinomas and normal mucosa were analyzed for the methylation status of the MLH1 CpG island. Quantitative RT-PCR (TaqMan®) analyses of the expression levels of MLH1 normalized to ACTB (β-actin) was investigated. Furthermore, the microsatellite instability (MSI) status of each sample was analyzed by PCR of the BAT25 and BAT26 loci (Parsons et al., *Cancer Res.* 55:5548–5550, 1995). The twenty-five paired tumor and normal mucosal tissue samples were obtained from 25 patients with primary colorectal adenocarcinoma. The patients comprised 16 males and 9 females, ranging in age from 39–88 years, with a mean age of 68.8. The mucosal distance from tumor to normal specimens was between 10 and 20 cm. Approximately 2 grams of the surgically removed tissue was immediately frozen in liquid nitrogen and stored at −80° C. until RNA and DNA isolation.

Quantitative RT-PCR and Microsatellite Instability Analysis. The quantitation of mRNA levels was carried out using real-time fluorescence detection. The TaqMan® reactions were performed as described above for the assay, but with the addition of 1U AmpErase uracil N-glycosylase). After RNA isolation, cDNA was prepared from each sample as previously described (Bender et al., *Cancer Res* 58:95–101, 1998). Briefly, RNA was isolated by lysing tissue in buffer containing quanidine isothiocyanate (4M), N-lauryl sarcosine (0.5%), sodium citrate (25mM), and 2-mercaptoethanol (0.1M), followed by standard phenol-chloroform extraction, and precipitation in 50% isopropanol/50% lysis buffer. To prepare cDNA, RNA samples were reverse-transcribed using random hexamers, deoxynucleotide triphosphates, and Superscript II® reverse transcriptase (Life Technologies, Inc., Palo Alto, Calif.). The resulting cDNA was then amplified with primers specific for MLH1 and ACTB. Contamination of the RNA samples by genomic DNA was excluded by analysis of all RNA samples without prior cDNA conversion. Relative gene expression was determined based on the threshold cycles (number of PCR cycles required for detection with a specific probe) of the MLH1 gene and of the internal reference gene ACTB. The forward primer, probe and reverse primer sequences of the ACTB and MLH1 genes are: ACTB (TGAGCGCGGCTACAGCTT [SEQ ID NO. 25], 6FAM5'-ACCACCACGGCCGAGCGG-3'TAMRA [SEQ ID NO. 26], CCTTAATGTCACACACGATT [SEQ ID NO. 27]); and MLH1 (GTTCTCCGGGAGATGTTGCATA [SEQ ID NO. 28], 6FAM5'-CCTCAGTGGGCCTTGGCACAGC-3'TAMRA [SEQ ID NO. 29], TGGTGGTGTTGAGAAG-GTATAACTTG [SEQ ID NO. 30]).

Alterations of numerous polyadenine ("pA") sequences, distributed widely throughout the genome, is a useful characteristic to define tumors with microsatellite instability (Ionov et al., *Nature* 363:558–561, 1993). Microsatellite instability (MSI) was determined by PCR and sequence analysis of the BAT25 (25-base pair pA tract from an intron of the c-kit oncogene) and BAT26 (26-base pair pA tract from an intron of the mismatch repair gene hMSH2) loci as previously described (Parsons et al., *Cancer Res* 55:5548–5550, 1995). Briefly, segments the BAT25 and BAT26 loci were amplified for 30 cycles using one $^{32}$P-labeled primer and one unlabeled primer for each locus. Reactions were resolved on urea-formamide gels and exposed to film. The forward and reverse primers that were used for the amplification of BAT25 and BAT26 were: BAT25 (TCGCCTCCAAGAATGTAAGT [SEQ ID NO. 31], TCTGCATTTTAACTATGGCTC [SEQ ID NO. 32]); and BAT26 (TGACTACTTTTGACTTCAGCC [SEQ ID NO. 33], AACCATTCAACATTTTTAACCC [SEQ ID NO. 34]).

Figure 8:
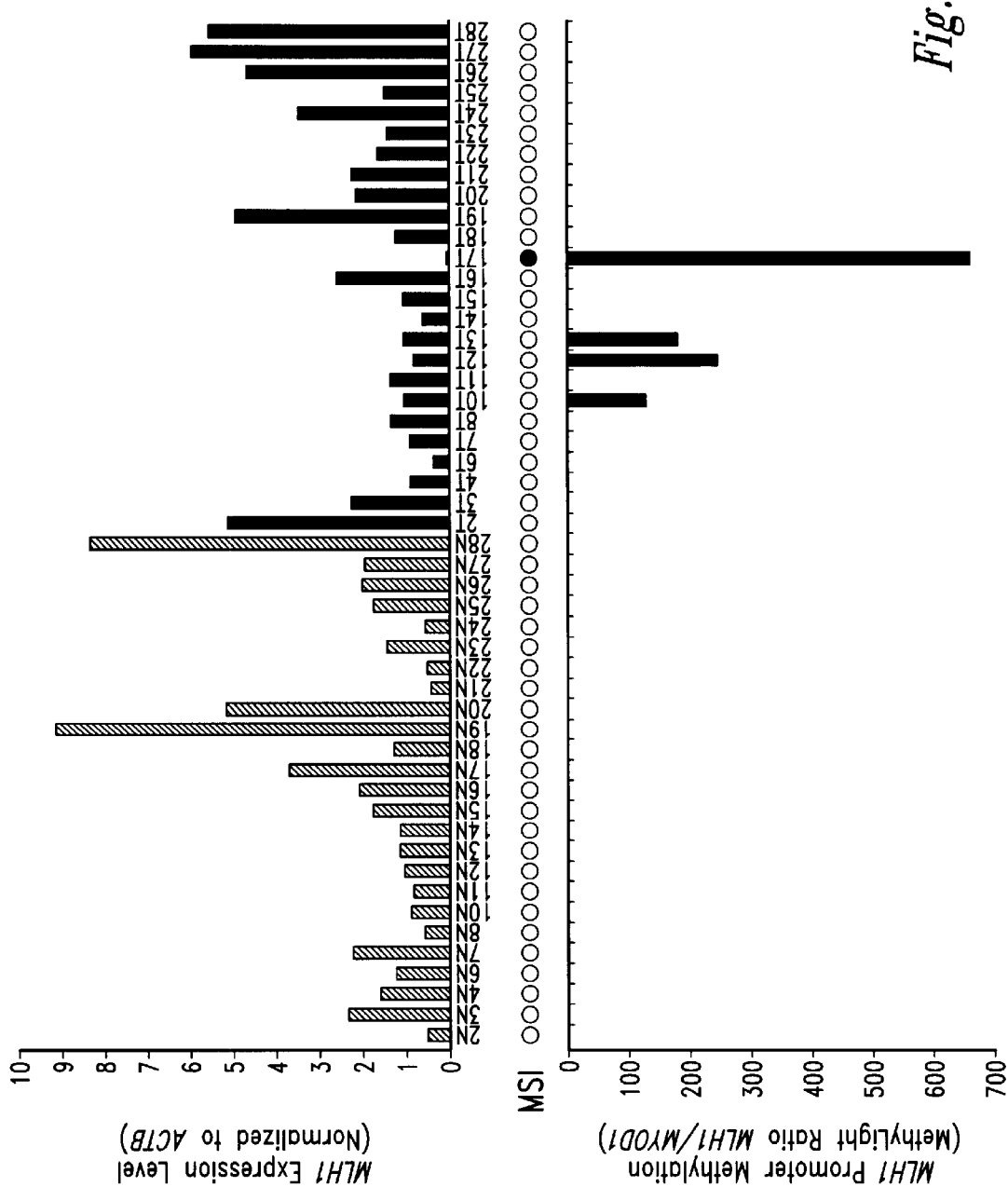
FIG. 8 illustrates a comparison of MLH1 expression, microsatellite instability and MLH1 promoter methylation of 25 matched-paired human colorectal samples. The upper chart shows the MLH1 expression levels measured by quantitative, real time RT-PCR (TaqMan®) in matched normal (hatched bars) and tumor (solid black bars) colorectal samples. The expression levels are displayed as a ratio between MLH1 and ACTB measurements. Microsatellite instability status (MSI) is indicated by the circles located between the two charts. A black circle denotes MSI positivity, while an open circle indicates that the sample is MSI negative, as determined by analysis of the BAT25 and BAT26 loci. The lower chart shows the methylation status of the MLH1 locus as determined by an inventive process. The methylation levels are represented as the ratio between the MLH1 methylated reaction and the MYOD1 reaction.

FIG. 8 shows the correlation between MLH1 gene expression, MSI status and promoter methylation of MLH1, as determined by the inventive process. The upper chart shows the MLH1 expression levels measured by quantitative, real time RT-PCR (TaqMan®) in matched normal (hatched bars) and tumor (solid black bars) colorectal samples. The expression levels are displayed as a ratio between MLH1 and ACTB measurements. Microsatellite instability status (MSI) is indicated by the circles located between the two charts. A black circle denotes MSI positivity, while an open circle indicates that the sample is MSI negative, as determined by analysis of the BAT25 and BAT26 loci. The lower chart shows the methylation status of the MLH1 locus as determined by inventive process. The methylation levels are represented as the ratio between the MLH1 methylated reaction and the MYOD1 reaction.

Four colorectal tumors had significantly elevated methylation levels compared to the corresponding normal tissue. One of these (tumor 17) exhibited a particularly high degree of MLH1 methylation, as scored by the inventive process. Tumor 17 was the only sample that was both MSI positive (black circle) and showed transcriptional silencing of MLH1. The remaining methylated tumors expressed MLH1 at modest levels and were MSI negative (white circle). These results show that MLH1 was biallelically methylated in tumor 17, resulting in epigenetic silencing and consequent microsatellite instability, whereas the other tumors showed lesser degrees of MLH1 promoter hypermethylation and could have just one methylated allele, allowing expression from the unaltered allele. Accordingly, the inventive process was capable of rapidly generating significant biological information, such as promoter CpG island hypermethylation in human tumors, which is associated with the transcriptional silencing of genes relevant to the cancer process.

We claim:

1. A method for detecting cytosine methylation and methylated CpG islands within a genomic sample of DNA comprising:
    (a) contacting a genomic sample of DNA with a modifying agent that modifies unmethylated cytosine to produce a converted nucleic acid;
    (b) amplifying the converted nucleic acid by means of oligonucleotide primers in the presence of one or a plurality of specific oligonucleotide probes, wherein one or a plurality of the oligonucleotide primers or the specific probe(s) are capable of distinguishing between unmethylated and methylated nucleic acid, with the proviso that at least one oligonucleotide probe is a CpG-specific probe capable of distinguishing between unmethylated and methylated nucleic acid; and
    (c) detecting the methylated nucleic acid based on amplification-mediated displacement of the CpG-specific probe.

2. The method of claim 1 wherein the amplifying step is a polymerase chain reaction (PCR).

3. The method of claim 1 wherein the modifying agent is bisulfite.

4. The method of claim 1 wherein the converted nucleic acid contains uracil in place of unmethylated cytosine residues present in the unmodified nucleic acid-containing sample.

5. The method of claim 1 wherein the probe further comprises one or a plurality of fluorescence label moieties.

6. The method of claim 5 wherein the amplification and detection step comprises fluorescence-based quantitative PCR.

7. A method for detecting a methylated CpG-containing nucleic acid comprising:
    (a) contacting a nucleic acid-containing sample with a modifying agent that modifies unmethylated cytosine to produce a converted nucleic acid;
    (b) amplifying the converted nucleic acid in the sample by means of oligonucleotide primers in the presence of a CpG-specific oligonucleotide probe, wherein the CpG-specific probe, but not the primers, distinguishes between modified unmethylated and methylated nucleic acid; and
    (c) detecting the methylated nucleic acid based upon an amplification-mediated displacement of the CpG-specific probe.

8. The method of claim 7 wherein the amplifying step comprises a polymerase chain reaction (PCR).

9. The method of claim 7 wherein the modifying agent comprises bisulfite.

10. The method of claim 7 wherein the converted nucleic acid contains uracil in place of unmethylated cytosine residues present in the unmodified nucleic acid-containing sample.

11. The method of claim 7 wherein the detection method is by means of a measurement of a fluorescence signal based on amplification-mediated displacement of the CpG-specific probe.

12. The method of claim 7 wherein the amplification and detection method comprises fluorescence-based quantitative PCR.

13. The method of claim 7 wherein methylation amounts in the nucleic acid sample are quantitatively determined based on reference to a control reaction for amount of input nucleic acid.

14. A method for detecting a methylated CpG-containing nucleic acid comprising:
    (a) contacting a nucleic acid-containing sample with a modifying agent that modifies unmethylated cytosine to produce a converted nucleic acid;
    (b) amplifying the converted nucleic acid in the sample by means of oligonucleotide primers in the presence of a CpG-specific oligonucleotide probe, wherein both the primers and the CpG-specific probe distinguish between modified unmethylated and methylated nucleic acid; and
    (c) detecting the methylated nucleic acid based on amplification-mediated displacement of the CpG-specific probe.

15. The method of claim 14 wherein the amplifying step comprises a polymerase chain reaction (PCR).

16. The method of claim 14 wherein the modifying agent is bisulfite.

17. The method of claim 14 wherein the converted nucleic acid contains uracil in place of unmethylated cytosine residues present in the unmodified nucleic acid-containing sample.

18. The method of claim 14 wherein the detection method comprises measuring a fluorescence signal based on amplification-mediated displacement of the CpG-specific probe.

19. The method of claim 14 wherein the amplification and detection method is fluorescence-based quantitative PCR.

20. A methylation detection kit useful for the detection of a methylated CpG-containing nucleic acid comprising a carrier means being compartmentalized to receive in close confinement therein one or more containers comprising:
    (i) a first container containing a modifying agent that modifies unmethylated cytosine to produce a converted nucleic acid;
    (ii) a second container containing primers for amplification of the converted nucleic acid;
    (iii) a third container containing primers for the amplification of control unmodified nucleic acid; and
    (iv) a fourth container containing a specific oligonucleotide probe the detection of which is based on amplification-mediated displacement, wherein the specific oligonucleotide probe is a CpG-specific oligonucleotide probe that distinguishes between modified unmethylated and methylated nucleic acid, and wherein the primers may or may not distinguish between unmethylated and methylated nucleic acid.

21. The kit of claim 20, wherein the modifying agent is bisulfite.

22. The kit of claim 20 wherein the modifying agent converts cytosine residues to uracil residues.

23. The kit of claim 20, wherein the CpG-specific oligonucleotide probe, but not the primers for amplification of the converted nucleic acid, distinguishes between modified unmethylated and methylated nucleic acid.

24. The kit of claim 20, wherein both the CpG-specific oligonucleotide probe and the primers for amplification of the converted nucleic acid, distinguish between modified unmethylated and methylated nucleic acid.

25. The kit of claim 20, wherein the CpG-specific probe further comprises a fluorescent moiety linked to an oligonucleotide base directly or through a linker moiety.

26. The kit of claim 20, wherein the CpG-specific probe is a specific, dual-labeled TaqMan® probe.

* * * * *

UNITED STATES PATENT AND TRADEMARK OFFICE
CERTIFICATE OF CORRECTION

PATENT NO.    : 6,331,393 B1
DATED         : December 18, 2001
INVENTOR(S)   : Peter W. Laird et al.

It is certified that error appears in the above-identified patent and that said Letters Patent is hereby corrected as shown below:

<u>Column 1,</u>
Line 12, the following should be inserted:
 This invention was made with government support under Grant Nos. R01 CA 75090 and R01 CA 71716 awarded by the NIH/NCI. The United States government has certain rights in the invention.

Signed and Sealed this

Twenty-eighth Day of May, 2002

*Attest:*

JAMES E. ROGAN
*Attesting Officer*    *Director of the United States Patent and Trademark Office*

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (iii) HYPOTHETICAL: No (xi) SEQUENCE DESCRIPTION: SEQ ID NO:1:

GGCGTTCGTT TTGGGATTG                                                19

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (iii) HYPOTHETICAL: No (ix) FEATURE:
       (A) NAME/KEY: 5' substitution with fluorescent reporter
           dye 6FAM (2,7-dimethoxy-4,5-dichloro-6-carboxy-
           fluorescein-phosporamidite-cytosine); 3'substitution
           with quencher dye TAMRA (6-carboxytetramethylrhodamine).

(xi) SEQUENCE DESCRIPTION: SEQ ID NO:2:

CGATAAAACC GAACGACCCG ACGA                                          24

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (iii) HYPOTHETICAL: No (xi) SEQUENCE DESCRIPTION: SEQ ID NO:3:

GCCGACACGC GAACTCTAA                                                19

(2) INFORMATION FOR SEQ ID NO:4:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (iii) HYPOTHETICAL: No (xi) SEQUENCE DESCRIPTION: SEQ ID NO:4:

```
ACACATATCC CACCAACACA CAA                                            23

(2) INFORMATION FOR SEQ ID NO:5:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (ix) FEATURE:
        (A) NAME/KEY: 5' substitution with fluorescent reporter
            dye 6FAM (2,7-dimethoxy-4,5-dichloro-6-carboxy-
            fluorescein-phosporamidite-cytosine); 3'substitution
            with quencher dye TAMRA (6-carboxytetramethylrhodamine).

(xi) SEQUENCE DESCRIPTION: SEQ ID NO:5:

CAACCCTACC CCAAAAACCT ACAAATCCAA                                     30

(2) INFORMATION FOR SEQ ID NO:6:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:6:

AGGAGTTGGT GGAGGGTGTT T                                              21

(2) INFORMATION FOR SEQ ID NO:7:

(i) SEQUENCE CHARACTERISTICS:
        (A) LENGTH:  18 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:7:

CTATCGCCGC CTCATCGT                                                  18

(2) INFORMATION FOR SEQ ID NO:8:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (ix) FEATURE:
        (A) NAME/KEY: 5' substitution with fluorescent reporter
            dye 6FAM (2,7-dimethoxy-4,5-dichloro-6-carboxy-
            fluorescein-phosporamidite-cytosine); 3'substitution with
            quencher dye TAMRA (6-carboxytetramethylrhodamine).

(xi) SEQUENCE DESCRIPTION: SEQ ID NO:8:
```

CGCGACGTCA AACGCCACTA CG                                                22

(2) INFORMATION FOR SEQ ID NO:9:

(i) SEQUENCE CHARACTERISTICS:
        (A) LENGTH:   30 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:9:

CGTTATATAT CGTTCGTAGT ATTCGTGTTT                                         30

(2) INFORMATION FOR SEQ ID NO:10:

(i) SEQUENCE CHARACTERISTICS:
        (A) LENGTH:   27 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:10:

TTATATGTCG GTTACGTGCG TTTATAT                                            27

(2) INFORMATION FOR SEQ ID NO:11:

(i) SEQUENCE CHARACTERISTICS:
        (A) LENGTH:   22 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (ix) FEATURE:
        (A) NAME/KEY: 5' substitution with fluorescent reporter
            dye 6FAM (2,7-dimethoxy-4,5-dichloro-6-carboxy-
            fluorescein-phosporamidite-cytosine); 3'substitution with
            quencher dye TAMRA (6-carboxytetramethylrhodamine).

(xi) SEQUENCE DESCRIPTION: SEQ ID NO:11:

CCCGTCGAAA ACCCGCCGAT TA                                                 22

(2) INFORMATION FOR SEQ ID NO:12:

(i) SEQUENCE CHARACTERISTICS:
        (A) LENGTH:   19 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:12:

GAACCAAAAC GCTCCCCAT                                                     19

(2) INFORMATION FOR SEQ ID NO:13:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (iii) HYPOTHETICAL: No (xi) SEQUENCE DESCRIPTION: SEQ ID NO:13:

GGGTTGTGAG GGTATATTTT TGAGG                                                25

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: No (ix) FEATURE:
        (A) NAME/KEY: 5' substitution with fluorescent reporter
            dye 6FAM (2,7-dimethoxy-4,5-dichloro-6-carboxy-
            fluorescein-phosporamidite-cytosine); 3'substitution with
            quencher dye TAMRA (6-carboxytetramethylrhodamine).

(xi) SEQUENCE DESCRIPTION: SEQ ID NO:14:

CCCACCCAAC CACACAACCT ACCTAACC                                             28

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: No (xi) SEQUENCE DESCRIPTION: SEQ ID NO:15:

CCAACCCACA CTCCACAATA AA                                                   22

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: No (xi) SEQUENCE DESCRIPTION: SEQ ID NO:16:

AACAACGTCC GCACCTCCT                                                       19

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single (D) TOPOLOGY:  linear (ii) MOLECULE TYPE:  DNA (iii) HYPOTHETICAL:  No (ix) FEATURE:
          (A) NAME/KEY: 5' substitution with fluorescent reporter
              dye 6FAM (2,7-dimethoxy-4,5-dichloro-6-carboxy-
              fluorescein-phosporamidite-cytosine); 3'substitution with
              quencher dye TAMRA (6-carboxytetramethylrhodamine).

(xi) SEQUENCE DESCRIPTION: SEQ ID NO:17:

ACCCGACCCC  GAACCGCG                                                18

(2) INFORMATION FOR SEQ ID NO:18:

(i) SEQUENCE CHARACTERISTICS:
          (A) LENGTH:  22 base pairs
          (B) TYPE:  nucleic acid
          (C) STRANDEDNESS:  single
          (D) TOPOLOGY:  linear (ii) MOLECULE TYPE:  DNA (iii) HYPOTHETICAL:  No (xi) SEQUENCE DESCRIPTION: SEQ ID NO:18:

TGGAATTTTC GGTTGATTGG TT                                            22

(2) INFORMATION FOR SEQ ID NO:19:

(i) SEQUENCE CHARACTERISTICS:
          (A) LENGTH:  24 base pairs
          (B) TYPE:  nucleic acid
          (C) STRANDEDNESS:  single
          (D) TOPOLOGY:  linear (ii) MOLECULE TYPE:  DNA (iii) HYPOTHETICAL:  No (xi) SEQUENCE DESCRIPTION: SEQ ID NO:19:

CAACCAATCA ACCAAAAATT CCAT                                          24

(2) INFORMATION FOR SEQ ID NO:20:

(i) SEQUENCE CHARACTERISTICS:
          (A) LENGTH:  28 base pairs
          (B) TYPE:  nucleic acid
          (C) STRANDEDNESS:  single
          (D) TOPOLOGY:  linear (ii) MOLECULE TYPE:  DNA (iii) HYPOTHETICAL:  No (ix) FEATURE:
          (A) NAME/KEY: 5' substitution with fluorescent reporter
              dye 6FAM (2,7-dimethoxy-4,5-dichloro-6-carboxy-
              fluorescein-phosporamidite-cytosine); 3'substitution with
              quencher dye TAMRA (6-carboxytetramethylrhodamine).

(xi) SEQUENCE DESCRIPTION: SEQ ID NO:20:

CCACCACCCA CTATCTACTC TCCCCCTC                                      28

(2) INFORMATION FOR SEQ ID NO:21:

(i) SEQUENCE CHARACTERISTICS:
          (A) LENGTH:  22 base pairs
          (B) TYPE:  nucleic acid

```
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:21:

GGTGGATTGT GTGTGTTTGG TG                                              22

(2) INFORMATION FOR SEQ ID NO:22:

(i) SEQUENCE CHARACTERISTICS:
            (A) LENGTH:  23 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:22:

CCAACTCCAA ATCCCCTCTC TAT                                             23

(2) INFORMATION FOR SEQ ID NO:23:

(i) SEQUENCE CHARACTERISTICS:
            (A) LENGTH:  36 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (ix) FEATURE:
            (A) NAME/KEY: 5' substitution with fluorescent reporter
                dye 6FAM (2,7-dimethoxy-4,5-dichloro-6-carboxy-
                fluorescein-phosporamidite-cytosine); 3'substitution with
                quencher dye TAMRA (6-carboxytetramethylrhodamine).

(xi) SEQUENCE DESCRIPTION: SEQ ID NO:23:

TCCCTTCCTA TTCCTAAATC CAACCTAAAT ACCTCC                               36

(2) INFORMATION FOR SEQ ID NO:24:

(i) SEQUENCE CHARACTERISTICS:
            (A) LENGTH:  30 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:24:

TGATTAATTT AGATTGGGTT TAGAGAAGGA                                      30

(2) INFORMATION FOR SEQ ID NO:25:

(i) SEQUENCE CHARACTERISTICS:
            (A) LENGTH:  18 base pairs
            (B) TYPE:  nucleic acid
            (C) STRANDEDNESS:  single
            (D) TOPOLOGY:  linear (ii) MOLECULE TYPE:  DNA
```

```
      (iii) HYPOTHETICAL:  No (xi) SEQUENCE DESCRIPTION: SEQ ID NO:25:

TGAGCGCGGC TACAGCTT                                                       18

(2) INFORMATION FOR SEQ ID NO:26:

(i) SEQUENCE CHARACTERISTICS:
           (A) LENGTH:  18 base pairs
           (B) TYPE:  nucleic acid
           (C) STRANDEDNESS:  single
           (D) TOPOLOGY:  linear (ii) MOLECULE TYPE:  DNA (iii) HYPOTHETICAL:  No (ix) FEATURE:
           (A) NAME/KEY: 5' substitution with fluorescent reporter
               dye 6FAM (2,7-dimethoxy-4,5-dichloro-6-carboxy-
               fluorescein-phosporamidite-cytosine); 3'substitution with
               quencher dye TAMRA (6-carboxytetramethylrhodamine).

(xi) SEQUENCE DESCRIPTION: SEQ ID NO:26:

ACCACCACGG CCGAGCGG                                                       18

(2) INFORMATION FOR SEQ ID NO:27:

(i) SEQUENCE CHARACTERISTICS:
           (A) LENGTH:  20 base pairs
           (B) TYPE:  nucleic acid
           (C) STRANDEDNESS:  single
           (D) TOPOLOGY:  linear (ii) MOLECULE TYPE:  DNA (iii) HYPOTHETICAL:  No (xi) SEQUENCE DESCRIPTION: SEQ ID NO:27:

CCTTAATGTC ACACACGATT                                                     20

(2) INFORMATION FOR SEQ ID NO:28:

(i) SEQUENCE CHARACTERISTICS:
           (A) LENGTH:  22 base pairs
           (B) TYPE:  nucleic acid
           (C) STRANDEDNESS:  single
           (D) TOPOLOGY:  linear (ii) MOLECULE TYPE:  DNA (iii) HYPOTHETICAL:  No (xi) SEQUENCE DESCRIPTION: SEQ ID NO:28:

GTTCTCCGGG AGATGTTGCA TA                                                  22

(2) INFORMATION FOR SEQ ID NO:29:

(i) SEQUENCE CHARACTERISTICS:
           (A) LENGTH:  22 base pairs
           (B) TYPE:  nucleic acid
           (C) STRANDEDNESS:  single
           (D) TOPOLOGY:  linear (ii) MOLECULE TYPE:  DNA (iii) HYPOTHETICAL:  No (ix) FEATURE:
           (A) NAME/KEY: 5' substitution with fluorescent reporter
               dye 6FAM (2,7-dimethoxy-4,5-dichloro-6-carboxy-
``` fluorescein-phosporamidite-cytosine); 3'substitution with
              quencher dye TAMRA (6-carboxytetramethylrhodamine).

(xi) SEQUENCE DESCRIPTION: SEQ ID NO:29:

CCTCAGTGGG CCTTGGCACA GC                                              22

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: No (xi) SEQUENCE DESCRIPTION: SEQ ID NO:30:

TGGTGGTGTT GAGAAGGTAT AACTTG                                          26

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: No (x) PUBLICATION INFORMATION:
        (A) AUTHORS: Parsons, et al
        (B) TITLE: Microsatellite Instability and Mutations of the
            Transforming Growth Factor B Type II Receptor Gene in
            Colorectal Cancer
        (C) JOURNAL: Cancer Res.
        (D) VOLUME: 55
        (F) PAGES: 5548-5550
        (G) DATE: 01-DEC-1995

(xi) SEQUENCE DESCRIPTION: SEQ ID NO:31:

TCGCCTCCAA GAATGTAAGT                                                 20

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: No (x) PUBLICATION INFORMATION:
        (A) AUTHORS: Parsons, et al
        (B) TITLE: Microsatellite Instability and Mutations of
            the Transforming Growth Factor B Type II Receptor Gene
            in Colorectal Cancer
        (C) JOURNAL: Cancer Res.
        (D) VOLUME: 55
        (F) PAGES: 5548-5550
        (G) DATE: 01-DEC-1995

(xi) SEQUENCE DESCRIPTION: SEQ ID NO:32:

TCTGCATTTT AACTATGGCT C                                               21

-continued (2) INFORMATION FOR SEQ ID NO:33:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (x) PUBLICATION INFORMATION:
        (A) AUTHORS:  Parsons, et al
        (B) TITLE:  Microsatellite Instability and Mutations of
            the Transforming Growth Factor B Type II Receptor Gene
            in Colorectal Cancer
        (C) JOURNAL: Cancer Res.
        (D) VOLUME:  55
        (F) PAGES:  5548-5550
        (G) DATE:  01-DEC-1995

(xi) SEQUENCE DESCRIPTION: SEQ ID NO:33:

TGACTACTTT TGACTTCAGC C                                      21

(2) INFORMATION FOR SEQ ID NO:34:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (x) PUBLICATION INFORMATION:
        (A) AUTHORS:  Parsons, et al
        (B) TITLE:  Microsatellite Instability and Mutations of the
            Transforming Growth Factor B Type II Receptor Gene in
            Colorectal Cancer
        (C) JOURNAL: Cancer Res.
        (D) VOLUME:  55
        (F) PAGES:  5548-5550
        (G) DATE:  01-DEC-1995

(xi) SEQUENCE DESCRIPTION: SEQ ID NO:34:

AACCATTCAA CATTTTTAAC CC                                  22

(2) INFORMATION FOR SEQ ID NO:35:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:35:

TCCTAAAACT ACACTTACTC C                                      21

(2) INFORMATION FOR SEQ ID NO:36:

(i) SEQUENCE CHARACTERISTICS:
        (A) LENGTH:  23 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:36:

GGTTATTTGG AAAAAGAGTA TAG                                                  23

(2) INFORMATION FOR SEQ ID NO:37:

(i) SEQUENCE CHARACTERISTICS:
            (A) LENGTH:   22 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:37:

AGAGAGAAGT AGTTGTGTTA AT                                                   22

(2) INFORMATION FOR SEQ ID NO:38:

(i) SEQUENCE CHARACTERISTICS:
            (A) LENGTH:   21 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:38:

ACTACACCAA TACAACCACA T                                                    21

(2) INFORMATION FOR SEQ ID NO:39:

(i) SEQUENCE CHARACTERISTICS:
            (A) LENGTH:   12 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:39:

AAACCAAAAC TC                                                              12

(2) INFORMATION FOR SEQ ID NO:40:

(i) SEQUENCE CHARACTERISTICS:
            (A) LENGTH:   16 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  No (xi) SEQUENCE DESCRIPTION: SEQ ID NO:40:

CCCACACCCA ACCAAT                                                          16

(2) INFORMATION FOR SEQ ID NO:41:

```
    (i) SEQUENCE CHARACTERISTICS:
        (A) LENGTH:  23 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:41:

GGAGGTTATA AGAGTAGGGT TAA                                              23

(2) INFORMATION FOR SEQ ID NO:42:

(i) SEQUENCE CHARACTERISTICS:
        (A) LENGTH:  24 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:42:

CCAACCAATA AAAACAAAAA TACC                                             24

(2) INFORMATION FOR SEQ ID NO:43:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:43:

GTAGGTGGGG AGGAGTTTAG TT                                               22

(2) INFORMATION FOR SEQ ID NO:44:

(i) SEQUENCE CHARACTERISTICS:
        (A) LENGTH:  23 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:44:

TCTAATAACC AACCAACCCC TCC                                              23

(2) INFORMATION FOR SEQ ID NO:45:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:45:
```

TTGTATTATT TTGTTTTTTT TGGTAGG                     27

(2) INFORMATION FOR SEQ ID NO:46:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:46:

CAACTTCTCA AATCATCAAT CCTCAC                      26

(2) INFORMATION FOR SEQ ID NO:47:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:47:

TTTAGTAGAG GTATATAAGT T                           21

(2) INFORMATION FOR SEQ ID NO:48:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:48:

TAAGGGGAGA GGAGGAGTTT GAGAAG                      26

(2) INFORMATION FOR SEQ ID NO:49:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (ii) MOLECULE TYPE:  DNA (iii) HYPOTHETICAL:  No (xi) SEQUENCE DESCRIPTION: SEQ ID NO:49:

TTTGAGGGAT AGGGT                                  15

(2) INFORMATION FOR SEQ ID NO:50:

(i) SEQUENCE CHARACTERISTICS:
        (A) LENGTH:  18 base pairs
        (B) TYPE:  nucleic acid
        (C) STRANDEDNESS:  single
        (D) TOPOLOGY:  linear (ii) MOLECULE TYPE: DNA (iii) HYPOTHETICAL: No (xi) SEQUENCE DESCRIPTION: SEQ ID NO:50:

TTTTAGGGGT GTTATATT                                              18

(2) INFORMATION FOR SEQ ID NO:51:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: No (xi) SEQUENCE DESCRIPTION: SEQ ID NO:51:

TTTTTTTGTT TGGAAAGATA T                                          21

(2) INFORMATION FOR SEQ ID NO:52:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (iii) HYPOTHETICAL: No (xi) SEQUENCE DESCRIPTION: SEQ ID NO:52:

GTTGGTGGTG TTGTAT                                                16

(2) INFORMATION FOR SEQ ID NO:53:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (iii) HYPOTHETICAL: No (xi) SEQUENCE DESCRIPTION: SEQ ID NO:53:

AGGTTATGAT GATGGGTAG                                             19

(2) INFORMATION FOR SEQ ID NO:54:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (iii) HYPOTHETICAL: No (xi) SEQUENCE DESCRIPTION: SEQ ID NO:54:

TATTAGAGGT AGTAATTATG TT                                         22